(12) United States Patent
Sezen et al.

(10) Patent No.: US 9,091,628 B2
(45) Date of Patent: Jul. 28, 2015

(54) 3D MAPPING WITH TWO ORTHOGONAL IMAGING VIEWS

(71) Applicant: L-3 Communications Security and Detection Systems, Inc., Woburn, MA (US)

(72) Inventors: Kumsal Deniz Sezen, Waltham, MA (US); Stephen Bushnell-Fowler, Clearwater, FL (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 230 days.

(21) Appl. No.: 13/724,397

(22) Filed: Dec. 21, 2012

(65) Prior Publication Data

US 2014/0175298 A1   Jun. 26, 2014

(51) Int. Cl.
| | | |
|---|---|---|
| *G01N 23/04* | (2006.01) | |
| *G01V 5/00* | (2006.01) | |
| *G01N 23/083* | (2006.01) | |
| *G01N 23/09* | (2006.01) | |

(52) U.S. Cl.
CPC .............. *G01N 23/04* (2013.01); *G01N 23/083* (2013.01); *G01N 23/09* (2013.01); *G01V 5/0016* (2013.01); *G01V 5/0041* (2013.01)

(58) Field of Classification Search
CPC ... G01N 23/083; G01N 23/09; G01V 5/0016; G01V 5/0041
USPC .............. 250/360.1, 358.1, 390.06; 378/57, 9
See application file for complete search history.

(56) References Cited

U.S. PATENT DOCUMENTS

| | | | |
|---|---|---|---|
| 4,075,700 A | | 2/1978 | Blay |
| 4,149,247 A | | 4/1979 | Pavkovich et al. |
| 4,149,248 A | | 4/1979 | Pavkovich |
| 4,294,544 A | | 10/1981 | Altschuler et al. |
| 4,326,252 A | | 4/1982 | Kohno et al. |
| 4,365,339 A | | 12/1982 | Pavkovich et al. |
| 4,468,694 A | | 8/1984 | Edgar |
| 4,486,835 A | | 12/1984 | Bai et al. |
| 4,539,639 A | | 9/1985 | Le Coq et al. |
| 4,562,540 A | | 12/1985 | Devaney |
| 4,594,662 A | | 6/1986 | Devaney |
| 4,598,366 A | | 7/1986 | Devaney |
| 4,674,046 A | | 6/1987 | Ozeki et al. |
| 4,709,382 A | | 11/1987 | Sones |
| 4,751,643 A | | 6/1988 | Lorensen et al. |
| 4,751,660 A | | 6/1988 | Hedley |
| 4,777,598 A | | 10/1988 | Kellar et al. |
| 4,791,567 A | | 12/1988 | Cline et al. |
| 4,791,934 A | | 12/1988 | Brunnett |
| 4,799,267 A | | 1/1989 | Kamejima et al. |
| 4,821,213 A | | 4/1989 | Cline et al. |
| 4,835,688 A | | 5/1989 | Kimura |
| 4,864,142 A | * | 9/1989 | Gomberg ................. 250/390.04 |
| 4,896,343 A | | 1/1990 | Saunders |
| 4,903,202 A | | 2/1990 | Crawford |
| 4,905,148 A | | 2/1990 | Crawford |
| 5,060,276 A | | 10/1991 | Morris et al. |
| 5,070,455 A | | 12/1991 | Singer et al. |
| 5,073,910 A | | 12/1991 | Eberhard et al. |

(Continued)

*Primary Examiner* — David Porta
*Assistant Examiner* — Mindy Vu
(74) *Attorney, Agent, or Firm* — Fish & Richardson P.C.

(57) ABSTRACT

Methods, systems, and apparatuses, including computer programs encoded on a computer storage medium, for generating location and size measurements for small scattered objects in a large medium are disclosed.

15 Claims, 7 Drawing Sheets

(56) References Cited

U.S. PATENT DOCUMENTS

| | | |
|---|---|---|
| 5,098,640 A | 3/1992 | Gozani et al. |
| 5,117,829 A | 6/1992 | Miller et al. |
| 5,127,037 A | 6/1992 | Bynum |
| 5,133,601 A | 7/1992 | Cohen et al. |
| 5,170,439 A | 12/1992 | Zeng et al. |
| 5,204,734 A | 4/1993 | Cohen et al. |
| 5,243,665 A | 9/1993 | Maney et al. |
| 5,247,561 A | 9/1993 | Kotowski |
| 5,283,837 A | 2/1994 | Wood |
| 5,333,164 A | 7/1994 | Tam |
| 5,333,165 A | 7/1994 | Sun |
| 5,355,221 A | 10/1994 | Cohen et al. |
| 5,365,560 A | 11/1994 | Tam |
| 5,367,552 A * | 11/1994 | Peschmann .................. 378/57 |
| 5,375,156 A | 12/1994 | Kuo-Petravic et al. |
| 5,390,226 A | 2/1995 | Tam |
| 5,400,255 A | 3/1995 | Hu |
| 5,402,460 A | 3/1995 | Johnson et al. |
| 5,408,511 A | 4/1995 | Grangeat et al. |
| 5,428,655 A | 6/1995 | Moriya et al. |
| 5,446,776 A | 8/1995 | Tam |
| 5,458,125 A | 10/1995 | Schweikard |
| 5,461,650 A | 10/1995 | Tam |
| 5,461,651 A | 10/1995 | Tam |
| 5,483,569 A | 1/1996 | Annis |
| 5,570,404 A | 10/1996 | Liang et al. |
| 5,576,948 A | 11/1996 | Stern et al. |
| 5,576,964 A | 11/1996 | Choate |
| 5,588,033 A | 12/1996 | Yeung |
| 5,590,169 A | 12/1996 | Monteiro |
| 5,635,709 A | 6/1997 | Sliski et al. |
| 5,638,461 A | 6/1997 | Fridge |
| 5,647,018 A | 7/1997 | Benjamin |
| 5,668,846 A | 9/1997 | Fox et al. |
| 5,684,898 A | 11/1997 | Brady et al. |
| 5,684,981 A | 11/1997 | Jones |
| 5,696,806 A | 12/1997 | Grodzins et al. |
| 5,699,799 A | 12/1997 | Xu et al. |
| 5,717,733 A | 2/1998 | Kurbatov et al. |
| 5,719,773 A | 2/1998 | Choate |
| 5,722,408 A | 3/1998 | Dehner et al. |
| 5,741,215 A | 4/1998 | D'Urso |
| 5,744,802 A | 4/1998 | Muehllehner et al. |
| 5,745,126 A | 4/1998 | Jain et al. |
| RE35,798 E | 5/1998 | Kimura |
| 5,751,844 A | 5/1998 | Bolin et al. |
| 5,754,704 A | 5/1998 | Barnsley et al. |
| 5,781,605 A | 7/1998 | Wohlrab |
| 5,791,346 A | 8/1998 | Craine et al. |
| 5,799,099 A | 8/1998 | Wang et al. |
| 5,802,134 A | 9/1998 | Larson et al. |
| 5,805,659 A | 9/1998 | Tam |
| 5,818,896 A | 10/1998 | Hsieh |
| 5,828,723 A | 10/1998 | Mariscotti |
| 5,838,759 A * | 11/1998 | Armistead .................. 378/57 |
| 5,839,440 A | 11/1998 | Liou et al. |
| 5,841,830 A | 11/1998 | Barni et al. |
| 5,848,114 A | 12/1998 | Kawai et al. |
| 5,848,115 A | 12/1998 | Little et al. |
| 5,852,646 A | 12/1998 | Klotz et al. |
| 5,852,672 A | 12/1998 | Lu |
| 5,862,198 A | 1/1999 | Samarasekera et al. |
| 5,864,632 A | 1/1999 | Ogawa et al. |
| 5,870,697 A | 2/1999 | Chandler et al. |
| 5,878,103 A | 3/1999 | Sauer et al. |
| 5,881,122 A | 3/1999 | Crawford et al. |
| 5,881,123 A | 3/1999 | Tam |
| 5,883,933 A | 3/1999 | Goto et al. |
| 5,887,047 A | 3/1999 | Bailey et al. |
| 5,901,195 A | 5/1999 | Sauer et al. |
| 5,901,196 A | 5/1999 | Sauer et al. |
| 5,909,476 A | 6/1999 | Cheng et al. |
| 5,909,477 A | 6/1999 | Crawford et al. |
| 5,926,521 A | 7/1999 | Tam |
| 5,930,326 A | 7/1999 | Rothschild et al. |
| 5,946,370 A | 8/1999 | Adler et al. |
| 5,960,055 A | 9/1999 | Samarasekera et al. |
| 5,963,612 A | 10/1999 | Navab |
| 5,963,613 A | 10/1999 | Navab |
| 5,970,111 A | 10/1999 | Samarasekera et al. |
| 5,995,580 A | 11/1999 | Schaller |
| 6,009,142 A | 12/1999 | Sauer et al. |
| 6,011,863 A | 1/2000 | Roy |
| 6,018,561 A | 1/2000 | Tam |
| 6,023,495 A | 2/2000 | Adler et al. |
| 6,028,907 A | 2/2000 | Adler et al. |
| 6,044,170 A | 3/2000 | Migdal et al. |
| 6,049,582 A | 4/2000 | Navab |
| 6,055,335 A | 4/2000 | Ida et al. |
| 6,061,469 A | 5/2000 | Walterman |
| 6,064,754 A | 5/2000 | Parekh et al. |
| 6,072,853 A | 6/2000 | Hall |
| 6,078,638 A | 6/2000 | Sauer et al. |
| 6,083,353 A | 7/2000 | Alexander, Jr. |
| 6,084,937 A | 7/2000 | Tam et al. |
| 6,097,784 A | 8/2000 | Tuy |
| 6,101,408 A | 8/2000 | Craine et al. |
| 6,104,775 A | 8/2000 | Tuy |
| 6,112,109 A | 8/2000 | D'Urso |
| 6,122,344 A | 9/2000 | Beevor |
| 6,141,398 A | 10/2000 | He et al. |
| 6,141,454 A | 10/2000 | Seymour et al. |
| 6,148,056 A | 11/2000 | Lin et al. |
| 6,160,910 A | 12/2000 | Freifeld |
| 6,160,914 A | 12/2000 | Muroya |
| 6,163,589 A | 12/2000 | Vartanian |
| 6,174,392 B1 | 1/2001 | Reis |
| 6,201,849 B1 | 3/2001 | Lai |
| 6,205,246 B1 | 3/2001 | Usami |
| 6,215,841 B1 | 4/2001 | Hsieh |
| 6,219,441 B1 | 4/2001 | Hu |
| 6,222,583 B1 | 4/2001 | Matsumura et al. |
| 6,229,913 B1 | 5/2001 | Nayar et al. |
| 6,233,303 B1 | 5/2001 | Tam |
| 6,236,704 B1 | 5/2001 | Navab et al. |
| 6,249,616 B1 | 6/2001 | Hashimoto |
| 6,256,367 B1 | 7/2001 | Vartanian |
| 6,275,615 B1 | 8/2001 | Ida et al. |
| 6,278,760 B1 | 8/2001 | Ogawa et al. |
| 6,278,794 B1 | 8/2001 | Parekh et al. |
| 6,282,260 B1 | 8/2001 | Grodzins |
| 6,292,525 B1 | 9/2001 | Tam |
| 6,301,496 B1 | 10/2001 | Reisfeld |
| 6,307,911 B1 | 10/2001 | Basu et al. |
| 6,307,959 B1 | 10/2001 | Mandelbaum et al. |
| 6,324,241 B1 | 11/2001 | Besson |
| 6,324,245 B1 | 11/2001 | Tam |
| 6,324,453 B1 | 11/2001 | Breed et al. |
| 6,330,298 B1 | 12/2001 | Tam |
| 6,333,960 B1 | 12/2001 | Tam |
| 6,341,153 B1 | 1/2002 | Rivera et al. |
| 6,343,108 B1 | 1/2002 | Heuscher |
| 6,356,653 B2 | 3/2002 | Brigante et al. |
| 6,368,285 B1 | 4/2002 | Osadchy et al. |
| 6,381,296 B1 | 4/2002 | Nishiura |
| 6,385,476 B1 | 5/2002 | Osadchy et al. |
| 6,400,843 B1 | 6/2002 | Shu et al. |
| 6,415,014 B1 | 7/2002 | Kim et al. |
| 6,424,735 B1 | 7/2002 | Freifeld |
| 6,438,259 B1 | 8/2002 | Anderson et al. |
| 6,442,465 B2 | 8/2002 | Breed et al. |
| 6,445,762 B1 | 9/2002 | Knoplioch et al. |
| 6,459,756 B1 | 10/2002 | Tam et al. |
| 6,463,116 B1 | 10/2002 | Oikawa |
| 6,473,488 B2 | 10/2002 | Menhardt |
| RE37,899 E | 11/2002 | Grodzins et al. |
| 6,480,618 B1 | 11/2002 | Parekh et al. |
| 6,483,948 B1 | 11/2002 | Spink et al. |
| 6,487,432 B2 | 11/2002 | Slack |
| 6,493,095 B1 | 12/2002 | Song et al. |
| 6,507,664 B1 | 1/2003 | Anderson et al. |
| 6,507,779 B2 | 1/2003 | Breed et al. |
| 6,516,046 B1 | 2/2003 | Frohlich et al. |
| 6,519,355 B2 | 2/2003 | Nelson |

(56) References Cited

U.S. PATENT DOCUMENTS

| | | |
|---|---|---|
| 6,522,775 B2 | 2/2003 | Nelson |
| 6,525,331 B1 | 2/2003 | Ngoi et al. |
| 6,542,573 B2 | 4/2003 | Schomberg |
| 6,546,073 B1 | 4/2003 | Lee |
| 6,549,288 B1 | 4/2003 | Migdal et al. |
| 6,553,296 B2 | 4/2003 | Breed et al. |
| 6,567,682 B1 | 5/2003 | Osterweil et al. |
| 6,570,952 B2 | 5/2003 | Paladini |
| 6,574,298 B2 | 6/2003 | Heuscher |
| 6,574,378 B1 | 6/2003 | Lim |
| 6,577,701 B2 | 6/2003 | Ukita et al. |
| 6,587,541 B2 | 7/2003 | Menhardt |
| 6,597,761 B1 | 7/2003 | Garms, III |
| 6,608,913 B1 | 8/2003 | Hinton et al. |
| 6,618,463 B1 | 9/2003 | Schotland et al. |
| 6,621,491 B1 | 9/2003 | Baumrind et al. |
| 6,628,984 B2 | 9/2003 | Weinberg |
| 6,636,623 B2 | 10/2003 | Nelson et al. |
| 6,643,351 B2 | 11/2003 | Morita et al. |
| 6,643,391 B2 | 11/2003 | Anderson et al. |
| 6,650,724 B2 | 11/2003 | Strobel |
| 6,658,142 B1 | 12/2003 | Kam et al. |
| 6,661,872 B2 | 12/2003 | Bova |
| 6,665,369 B2 | 12/2003 | Ukita |
| 6,665,555 B2 | 12/2003 | Henderson et al. |
| 6,668,036 B2 | 12/2003 | Numata et al. |
| 6,668,073 B1 | 12/2003 | Robar et al. |
| 6,687,393 B1 | 2/2004 | Skinner, Jr. |
| 6,690,762 B1 | 2/2004 | Berestov |
| 6,707,942 B1 | 3/2004 | Cortopassi et al. |
| 6,728,334 B1 | 4/2004 | Zhao |
| 6,735,331 B1 | 5/2004 | Binnun et al. |
| 6,741,674 B2 | 5/2004 | Lee |
| 6,744,848 B2 | 6/2004 | Stanton et al. |
| 6,751,283 B2 | 6/2004 | van de Haar |
| 6,754,297 B2 | 6/2004 | James |
| 6,757,426 B2 | 6/2004 | Link et al. |
| 6,757,445 B1 | 6/2004 | Knopp |
| 6,760,469 B1 | 7/2004 | Berestov et al. |
| 6,772,057 B2 | 8/2004 | Breed et al. |
| 6,778,850 B1 | 8/2004 | Adler et al. |
| 6,782,123 B1 | 8/2004 | Guillon et al. |
| 6,788,759 B2 | 9/2004 | Op De Beek et al. |
| 6,801,597 B2 | 10/2004 | Webber |
| 6,829,377 B2 | 12/2004 | Milioto |
| 6,839,400 B2 | 1/2005 | Bruder et al. |
| 6,850,586 B2 | 2/2005 | Cahill |
| 6,850,587 B1 | 2/2005 | Karimi et al. |
| 6,853,332 B1 | 2/2005 | Brookes |
| 6,853,912 B2 | 2/2005 | Han |
| 6,856,873 B2 | 2/2005 | Breed et al. |
| 6,862,334 B2 | 3/2005 | Van Liere et al. |
| 6,862,364 B1 | 3/2005 | Berestov |
| 6,865,246 B2 | 3/2005 | Yang |
| 6,865,289 B1 | 3/2005 | Berestov |
| 6,868,171 B2 | 3/2005 | Souluer |
| 6,880,387 B2 | 4/2005 | Kessler et al. |
| 6,885,939 B2 | 4/2005 | Schmidt et al. |
| 6,904,162 B2 | 6/2005 | Robar et al. |
| 6,907,100 B2 | 6/2005 | Taguchi |
| 6,909,800 B2 | 6/2005 | Vaidyanathan |
| 6,912,265 B2 | 6/2005 | Hebecker et al. |
| 6,914,613 B2 | 7/2005 | Marchand et al. |
| 6,931,093 B2 | 8/2005 | Op De Beek et al. |
| 6,944,259 B2 | 9/2005 | Yang |
| 6,947,038 B1 | 9/2005 | Anh et al. |
| 6,950,535 B2 | 9/2005 | Sibayama et al. |
| 6,961,404 B2 | 11/2005 | Cahill |
| 6,968,031 B2 | 11/2005 | Hinshaw |
| 6,970,593 B2 | 11/2005 | Furukawa |
| 6,973,156 B2 | 12/2005 | Sokolov |
| 6,983,034 B2 | 1/2006 | Wang et al. |
| 6,990,229 B2 | 1/2006 | Ohishi |
| 7,006,591 B2 | 2/2006 | Machida |
| 7,006,593 B2 | 2/2006 | Kokubun et al. |
| 7,010,080 B2 | 3/2006 | Mitschke et al. |
| 7,020,319 B2 | 3/2006 | Mertelmeier et al. |
| 7,027,143 B1 | 4/2006 | Stokowski et al. |
| 7,034,839 B2 | 4/2006 | Morishita |
| 7,039,238 B2 | 5/2006 | Sonmez et al. |
| 7,042,977 B2 | 5/2006 | Dafni |
| 7,043,057 B2 | 5/2006 | Retterath et al. |
| 7,043,080 B1 | 5/2006 | Dolan |
| 7,046,759 B2 | 5/2006 | Al-khalidy et al. |
| 7,046,762 B2 | 5/2006 | Lee |
| 7,065,234 B2 | 6/2006 | Du et al. |
| 7,065,242 B2 | 6/2006 | Petrov et al. |
| 7,068,752 B2 | 6/2006 | Brandt |
| 7,075,661 B2 | 7/2006 | Petty et al. |
| 7,103,135 B2 | 9/2006 | Koppe et al. |
| 7,106,885 B2 | 9/2006 | Osterweil et al. |
| 7,117,027 B2 | 10/2006 | Zheng et al. |
| 7,120,227 B2 | 10/2006 | Ozawa et al. |
| 7,123,356 B1 | 10/2006 | Stokowski et al. |
| 7,127,109 B1 | 10/2006 | Kim |
| 7,130,449 B2 | 10/2006 | Turner |
| 7,133,042 B2 | 11/2006 | Anh et al. |
| 7,133,539 B2 | 11/2006 | Ohto |
| 7,142,312 B2 | 11/2006 | Quadling et al. |
| 7,142,633 B2 | 11/2006 | Eberhard et al. |
| 7,149,346 B2 | 12/2006 | Oniyama |
| 7,162,064 B2 | 1/2007 | Klingenbeck-Regn |
| 7,173,251 B2 | 2/2007 | Fraser et al. |
| 7,180,976 B2 | 2/2007 | Wink et al. |
| 7,184,150 B2 | 2/2007 | Quadling et al. |
| 7,184,814 B2 | 2/2007 | Lang et al. |
| 7,218,758 B2 | 5/2007 | Ishii et al. |
| 7,227,981 B1 | 6/2007 | Fleute et al. |
| 7,231,087 B2 | 6/2007 | Huber |
| 7,233,683 B2 | 6/2007 | Han et al. |
| 7,239,908 B1 | 7/2007 | Alexander et al. |
| 7,242,791 B2 | 7/2007 | Han et al. |
| 7,265,754 B2 | 9/2007 | Brauss |
| 7,269,241 B2 | 9/2007 | Siltanen et al. |
| 7,274,812 B2 | 9/2007 | Saeki |
| 7,277,206 B2 | 10/2007 | Trifonov et al. |
| 7,286,246 B2 | 10/2007 | Yoshida |
| 7,286,866 B2 | 10/2007 | Okerlund et al. |
| 7,292,715 B2 | 11/2007 | Furnish |
| 7,308,297 B2 | 12/2007 | Reddy et al. |
| 7,315,605 B2 | 1/2008 | Boese et al. |
| 7,317,819 B2 | 1/2008 | Janes |
| 7,327,822 B2 | 2/2008 | Sauer et al. |
| 7,327,865 B2 | 2/2008 | Fu et al. |
| 7,327,872 B2 | 2/2008 | Vaillant et al. |
| 7,330,577 B2 | 2/2008 | Ernst et al. |
| 7,336,274 B2 | 2/2008 | Kida |
| 7,340,082 B2 | 3/2008 | Janssen et al. |
| 7,341,376 B2 | 3/2008 | Birdwell |
| 7,346,381 B2 | 3/2008 | Okerlund et al. |
| 7,356,113 B2 | 4/2008 | Wu et al. |
| 7,356,118 B2 | 4/2008 | Might et al. |
| 7,369,695 B2 | 5/2008 | Zettel et al. |
| 7,379,175 B1 | 5/2008 | Stokowski et al. |
| 7,386,089 B2 | 6/2008 | Endo et al. |
| 7,388,980 B2 | 6/2008 | Vaidyanathan |
| 7,403,315 B2 | 7/2008 | Tsuji et al. |
| 7,412,022 B2 | 8/2008 | Jupiter et al. |
| 7,415,126 B2 | 8/2008 | Breed et al. |
| 7,415,147 B2 | 8/2008 | Ying et al. |
| 7,418,079 B2 | 8/2008 | Schildkraut et al. |
| 7,421,101 B2 | 9/2008 | Georgescu et al. |
| 7,428,328 B2 | 9/2008 | Jee et al. |
| 7,433,507 B2 | 10/2008 | Jabri et al. |
| 7,440,535 B2 | 10/2008 | Netsch et al. |
| 7,446,899 B2 | 11/2008 | Matsuoka |
| 7,450,746 B2 | 11/2008 | Yang et al. |
| 7,453,456 B2 | 11/2008 | Petrov et al. |
| 7,463,772 B1 | 12/2008 | Lefevere et al. |
| 7,474,803 B2 | 1/2009 | Petrov et al. |
| 7,477,758 B2 | 1/2009 | Piirainen et al. |
| 7,492,862 B2 | 2/2009 | Bendahan |
| 7,496,226 B2 | 2/2009 | Negahdaripour et al. |
| 7,499,589 B1 | 3/2009 | Cortopassi et al. |

(56) References Cited

U.S. PATENT DOCUMENTS

| | | |
|---|---|---|
| 7,502,498 B2 | 3/2009 | Wen et al. |
| 7,505,561 B1 | 3/2009 | Fuller |
| 7,508,978 B1 | 3/2009 | Lefevere et al. |
| 7,515,769 B2 | 4/2009 | Akao et al. |
| 7,516,039 B2 | 4/2009 | McKitterick |
| 7,519,150 B2 | 4/2009 | Romesberg, III et al. |
| 7,526,063 B2 | 4/2009 | Boing et al. |
| 7,539,283 B2 | 5/2009 | Bendahan |
| 7,545,901 B2 | 6/2009 | Mistretta |
| 7,548,814 B2 | 6/2009 | Pantalone et al. |
| 7,552,008 B2 | 6/2009 | Newstrom et al. |
| 7,561,730 B2 | 7/2009 | Hewitson et al. |
| 7,565,190 B2 | 7/2009 | Okerlund et al. |
| 7,590,442 B2 | 9/2009 | Boese et al. |
| 7,593,555 B2 | 9/2009 | Spahn |
| 7,596,242 B2 | 9/2009 | Breed et al. |
| 7,596,287 B2 | 9/2009 | Wolf et al. |
| 7,609,875 B2 | 10/2009 | Liu et al. |
| 7,620,141 B2 | 11/2009 | Gotoh |
| 7,620,150 B1 | 11/2009 | Annis |
| 7,620,209 B2 | 11/2009 | Stevick et al. |
| 7,626,720 B2 | 12/2009 | Nakagawa |
| 7,627,172 B2 | 12/2009 | Urano et al. |
| 7,630,522 B2 | 12/2009 | Popp et al. |
| 7,634,112 B1 | 12/2009 | Lefevere et al. |
| 7,634,298 B2 | 12/2009 | Kaplan |
| 7,643,025 B2 | 1/2010 | Lange |
| 7,643,604 B2 | 1/2010 | Jupiter et al. |
| 7,643,609 B2 | 1/2010 | Clay |
| 7,643,654 B2 | 1/2010 | Fujiwara et al. |
| 7,643,673 B2 | 1/2010 | Rohlf et al. |
| 7,646,898 B1 | 1/2010 | Nowinski et al. |
| 7,646,900 B2 | 1/2010 | Movassaghi et al. |
| 7,655,895 B2 | 2/2010 | Breed |
| 7,660,437 B2 | 2/2010 | Breed |
| 7,676,062 B2 | 3/2010 | Breed et al. |
| 7,684,600 B2 | 3/2010 | Wang |
| 7,692,548 B2 | 4/2010 | Bonefas et al. |
| 7,692,549 B2 | 4/2010 | Bonefas et al. |
| 7,692,550 B2 | 4/2010 | Bonefas et al. |
| 7,692,551 B2 | 4/2010 | Bonefas et al. |
| 7,715,519 B2 | 5/2010 | Tsukagoshi et al. |
| 7,715,604 B2 | 5/2010 | Sun et al. |
| 7,715,608 B2 | 5/2010 | Vaz et al. |
| 7,724,931 B2 | 5/2010 | Kuth et al. |
| 7,724,932 B2 | 5/2010 | Ernst et al. |
| 7,738,626 B2 | 6/2010 | Weese et al. |
| 7,738,678 B2 | 6/2010 | Breed et al. |
| 7,738,695 B2 | 6/2010 | Shorte et al. |
| 7,747,047 B2 | 6/2010 | Okerlund et al. |
| 7,756,602 B2 | 7/2010 | Koempel et al. |
| 7,769,513 B2 | 8/2010 | Breed et al. |
| 7,778,454 B2 | 8/2010 | Grasruck et al. |
| 7,801,342 B2 | 9/2010 | Boese et al. |
| 7,804,980 B2 | 9/2010 | Sasaki |
| 7,804,981 B2 | 9/2010 | Viggiano et al. |
| 7,813,881 B2 | 10/2010 | Stein et al. |
| 7,825,925 B2 | 11/2010 | Voth |
| 7,831,076 B2 | 11/2010 | Altmann et al. |
| 7,831,094 B2 | 11/2010 | Gupta et al. |
| 7,831,358 B2 | 11/2010 | Breed et al. |
| 7,839,971 B2 | 11/2010 | Bendahan et al. |
| 7,844,027 B2 | 11/2010 | Harding et al. |
| 7,844,028 B2 | 11/2010 | Korsunsky |
| 7,848,593 B2 | 12/2010 | Murai et al. |
| 7,855,723 B2 | 12/2010 | Preiss et al. |
| 7,856,081 B2 * | 12/2010 | Peschmann .................. 378/57 |
| 7,860,300 B2 | 12/2010 | Siltanen et al. |
| 7,864,985 B1 | 1/2011 | Lefevere et al. |
| 7,865,006 B2 | 1/2011 | Hsieh et al. |
| 7,876,927 B2 | 1/2011 | Han et al. |
| 7,881,514 B2 | 2/2011 | Oaknin et al. |
| 7,903,856 B2 | 3/2011 | Pfister et al. |
| 7,912,271 B2 | 3/2011 | Hoppe et al. |
| 7,918,793 B2 | 4/2011 | Altmann et al. |
| 7,924,978 B2 | 4/2011 | Harding |
| 7,930,014 B2 | 4/2011 | Huennekens et al. |
| 7,933,445 B2 | 4/2011 | Pan et al. |
| 7,936,911 B2 | 5/2011 | Fang et al. |
| 7,940,260 B2 | 5/2011 | Kriveshko |
| 7,940,893 B2 | 5/2011 | Krauss |
| 7,961,912 B2 | 6/2011 | Stevick et al. |
| 7,961,934 B2 | 6/2011 | Thrun et al. |
| 7,966,058 B2 | 6/2011 | Xue et al. |
| 7,978,343 B2 | 7/2011 | Sun et al. |
| 7,980,378 B2 | 7/2011 | Jones et al. |
| 7,983,817 B2 | 7/2011 | Breed |
| 7,987,021 B2 | 7/2011 | Takaoka |
| 7,996,060 B2 | 8/2011 | Trofimov et al. |
| 8,000,445 B2 | 8/2011 | Mollus et al. |
| 8,005,314 B2 | 8/2011 | Ortyn et al. |
| 8,009,189 B2 | 8/2011 | Ortyn et al. |
| 8,009,885 B2 | 8/2011 | Grass et al. |
| 8,019,117 B2 | 9/2011 | Sasakawa |
| 8,023,698 B2 | 9/2011 | Niwa et al. |
| 8,027,526 B2 | 9/2011 | Boese et al. |
| 8,035,637 B2 | 10/2011 | Kriveshko |
| 8,036,734 B2 | 10/2011 | Schmidt |
| 8,041,131 B2 | 10/2011 | Li et al. |
| 8,050,461 B2 | 11/2011 | Shpunt et al. |
| 8,050,483 B2 | 11/2011 | Boese et al. |
| 8,050,489 B2 | 11/2011 | Eberle et al. |
| 8,050,496 B2 | 11/2011 | Pan et al. |
| 8,060,835 B2 | 11/2011 | Newcomer et al. |
| 8,064,068 B2 | 11/2011 | Fisher et al. |
| 8,064,571 B2 | 11/2011 | Thieberger et al. |
| 8,068,578 B2 | 11/2011 | Krauss |
| 8,068,648 B2 | 11/2011 | DiSilvestro et al. |
| 8,073,243 B2 | 12/2011 | Mareachen et al. |
| 8,077,955 B2 | 12/2011 | Dannels et al. |
| 8,090,174 B2 | 1/2012 | Navab |
| 8,090,194 B2 | 1/2012 | Golrdon et al. |
| 8,094,912 B2 | 1/2012 | Miyamoto et al. |
| 8,099,153 B2 | 1/2012 | Boese |
| 8,108,072 B2 | 1/2012 | Zhao et al. |
| 8,111,289 B2 | 2/2012 | Zruya et al. |
| 8,111,917 B2 | 2/2012 | Vogt et al. |
| 8,116,530 B2 | 2/2012 | Miyazaki |
| 8,126,236 B2 | 2/2012 | Harer et al. |
| RE43,282 E | 3/2012 | Alexander et al. |
| 8,130,221 B2 | 3/2012 | Voth |
| 8,131,042 B2 | 3/2012 | Tang et al. |
| 8,131,064 B2 | 3/2012 | Mashitani et al. |
| 8,132,728 B2 | 3/2012 | Dwinell et al. |
| 8,133,181 B2 | 3/2012 | Yuk et al. |
| 8,134,717 B2 | 3/2012 | Pangrazio et al. |
| 8,144,833 B2 | 3/2012 | Breedveld |
| 8,147,503 B2 | 4/2012 | Zhao et al. |
| 8,150,142 B2 | 4/2012 | Freedman et al. |
| 8,150,192 B2 | 4/2012 | Niemeyer et al. |
| 8,150,497 B2 | 4/2012 | Gielen et al. |
| 8,150,498 B2 | 4/2012 | Gielen et al. |
| 8,155,429 B2 | 4/2012 | Scholz et al. |
| 8,160,676 B2 | 4/2012 | Gielen et al. |
| 8,160,677 B2 | 4/2012 | Gielen et al. |
| 8,180,134 B2 | 5/2012 | Wang |
| 8,183,522 B2 | 5/2012 | Celi de la Torre et al. |
| 8,189,876 B2 | 5/2012 | Meredith et al. |
| 8,200,314 B2 | 6/2012 | Bladen et al. |
| 8,204,642 B2 | 6/2012 | Tanaka et al. |
| 8,208,719 B2 | 6/2012 | Gordon et al. |
| 8,218,843 B2 | 7/2012 | Edlauer et al. |
| 8,218,846 B2 | 7/2012 | Trumer et al. |
| 8,218,847 B2 | 7/2012 | Averbuch et al. |
| 2001/0026637 A1 | 10/2001 | Lelong et al. |
| 2001/0038681 A1 | 11/2001 | Stanton et al. |
| 2001/0043734 A1 | 11/2001 | Brigante et al. |
| 2001/0056234 A1 | 12/2001 | Weinberg |
| 2002/0001403 A1 | 1/2002 | Kikuchi |
| 2002/0018589 A1 | 2/2002 | Beuker et al. |
| 2002/0032378 A1 | 3/2002 | Henderson et al. |
| 2002/0044682 A1 | 4/2002 | Weil et al. |
| 2002/0076097 A1 | 6/2002 | Vaidyanathan |
| 2002/0076099 A1 | 6/2002 | Sakamoto et al. |

(56) References Cited

U.S. PATENT DOCUMENTS

| | | |
|---|---|---|
| 2002/0087274 A1 | 7/2002 | Alexander et al. |
| 2002/0097896 A1 | 7/2002 | Kuckendahl |
| 2002/0106051 A1 | 8/2002 | Menhardt |
| 2002/0131546 A1 | 9/2002 | Oikawa |
| 2002/0136447 A1 | 9/2002 | Link et al. |
| 2002/0141625 A1 | 10/2002 | Nelson |
| 2002/0150285 A1 | 10/2002 | Nelson |
| 2002/0168083 A1 | 11/2002 | Garms et al. |
| 2002/0172328 A1 | 11/2002 | Dekel |
| 2003/0031352 A1 | 2/2003 | Nelson et al. |
| 2003/0138077 A1 | 7/2003 | Lee |
| 2003/0160867 A1 | 8/2003 | Ohto et al. |
| 2003/0169926 A1 | 9/2003 | Sonmez et al. |
| 2004/0008875 A1 | 1/2004 | Linares |
| 2004/0042588 A1 | 3/2004 | Janes |
| 2004/0057608 A1 | 3/2004 | Souluer |
| 2004/0096096 A1 | 5/2004 | Huber |
| 2004/0105579 A1 | 6/2004 | Ishii et al. |
| 2004/0114800 A1 | 6/2004 | Ponomarev et al. |
| 2004/0120551 A1 | 6/2004 | Turner |
| 2004/0120560 A1 | 6/2004 | Robar et al. |
| 2004/0136571 A1 | 7/2004 | Hewitson et al. |
| 2004/0136578 A1 | 7/2004 | Sieracki et al. |
| 2004/0149021 A1 | 8/2004 | Kessler et al. |
| 2004/0151367 A1 | 8/2004 | Wolf et al. |
| 2004/0156531 A1 | 8/2004 | Retterath et al. |
| 2004/0161137 A1 | 8/2004 | Aben et al. |
| 2004/0165696 A1 | 8/2004 | Lee |
| 2004/0179729 A1 | 9/2004 | Imai et al. |
| 2004/0199064 A1 | 10/2004 | Van et al. |
| 2004/0223630 A1 | 11/2004 | Waupotitsch et al. |
| 2004/0247071 A1 | 12/2004 | Dafni |
| 2004/0247164 A1 | 12/2004 | Furnish |
| 2004/0249270 A1 | 12/2004 | Kondo et al. |
| 2004/0264762 A1 | 12/2004 | Mas et al. |
| 2004/0264763 A1 | 12/2004 | Mas et al. |
| 2005/0002488 A1 | 1/2005 | Ozawa et al. |
| 2005/0002544 A1 | 1/2005 | Winter et al. |
| 2005/0031197 A1 | 2/2005 | Knopp |
| 2005/0089212 A1 | 4/2005 | Mashitani et al. |
| 2005/0105679 A1 | 5/2005 | Wu et al. |
| 2005/0129305 A1 | 6/2005 | Chen et al. |
| 2005/0190881 A1 | 9/2005 | Obata et al. |
| 2005/0226482 A1 | 10/2005 | Kuduvalli |
| 2005/0238200 A1 | 10/2005 | Gupta et al. |
| 2005/0249388 A1 | 11/2005 | Linares |
| 2005/0271274 A1 | 12/2005 | Urano et al. |
| 2006/0008137 A1 | 1/2006 | Nagahdaripour et al. |
| 2006/0018509 A1 | 1/2006 | Miyoshi et al. |
| 2006/0018525 A1 | 1/2006 | Barbour |
| 2006/0039591 A1 | 2/2006 | Zettel et al. |
| 2006/0049930 A1 | 3/2006 | Zruya et al. |
| 2006/0056691 A1 | 3/2006 | Vaz et al. |
| 2006/0062446 A1 | 3/2006 | Porat |
| 2006/0078161 A1 | 4/2006 | Schmiegel et al. |
| 2006/0083422 A1 | 4/2006 | Ernst et al. |
| 2006/0088217 A1 | 4/2006 | Akoa et al. |
| 2006/0104406 A1 | 5/2006 | Siltanen et al. |
| 2006/0126921 A1 | 6/2006 | Shorte et al. |
| 2006/0153434 A1 | 7/2006 | Wang |
| 2006/0176998 A1 | 8/2006 | Korsunsky |
| 2006/0204070 A1 | 9/2006 | Hinshaw |
| 2006/0210134 A1 | 9/2006 | Grass et al. |
| 2006/0251293 A1 | 11/2006 | Piirainen et al. |
| 2006/0269108 A1 | 11/2006 | Viswanathan |
| 2006/0280336 A1 | 12/2006 | Lee |
| 2006/0285640 A1 | 12/2006 | Nizin et al. |
| 2007/0019840 A1 | 1/2007 | Fujiwara et al. |
| 2007/0025597 A1 | 2/2007 | Breed et al. |
| 2007/0047809 A1 | 3/2007 | Sasaki |
| 2007/0083108 A1 | 4/2007 | Boese et al. |
| 2007/0086624 A1 | 4/2007 | Breed et al. |
| 2007/0110289 A1 | 5/2007 | Fu et al. |
| 2007/0116341 A1 | 5/2007 | Fu et al. |
| 2007/0121779 A1 | 5/2007 | Nishide et al. |
| 2007/0122029 A1 | 5/2007 | Mowry |
| 2007/0145973 A1 | 6/2007 | Bertozzi et al. |
| 2007/0154063 A1 | 7/2007 | Breed |
| 2007/0172147 A1 | 7/2007 | Fujiwara et al. |
| 2007/0196815 A1 | 8/2007 | Lappe et al. |
| 2007/0211921 A1 | 9/2007 | Popp et al. |
| 2007/0223657 A1 | 9/2007 | Birdwell |
| 2007/0223794 A1 | 9/2007 | Preiss et al. |
| 2007/0262574 A1 | 11/2007 | Breed et al. |
| 2007/0263916 A1 | 11/2007 | Rasche et al. |
| 2007/0274440 A1 | 11/2007 | Sarment et al. |
| 2007/0274446 A1 | 11/2007 | Schildkraut et al. |
| 2007/0286342 A1 | 12/2007 | Fuller |
| 2008/0015433 A1 | 1/2008 | Alexander et al. |
| 2008/0016472 A1 | 1/2008 | Rohlf et al. |
| 2008/0019582 A1 | 1/2008 | Eberle et al. |
| 2008/0049898 A1 | 2/2008 | Romesberg et al. |
| 2008/0063299 A1 | 3/2008 | Murai et al. |
| 2008/0065291 A1 | 3/2008 | Breed |
| 2008/0068185 A1 | 3/2008 | Bonefas et al. |
| 2008/0068186 A1 | 3/2008 | Bonefas et al. |
| 2008/0068187 A1 | 3/2008 | Bonefas et al. |
| 2008/0069458 A1 | 3/2008 | Vega-Higuera et al. |
| 2008/0089557 A1 | 4/2008 | Iwaki et al. |
| 2008/0118143 A1 | 5/2008 | Gordon et al. |
| 2008/0130970 A1 | 6/2008 | Niemeyer et al. |
| 2008/0137927 A1 | 6/2008 | Altmann et al. |
| 2008/0144944 A1 | 6/2008 | Breed |
| 2008/0159473 A1 | 7/2008 | Clay |
| 2008/0166042 A1 | 7/2008 | Pan et al. |
| 2008/0166044 A1 | 7/2008 | Pan et al. |
| 2008/0170655 A1 | 7/2008 | Bendahan |
| 2008/0177163 A1 | 7/2008 | Wang et al. |
| 2008/0181357 A1 | 7/2008 | Bendahan |
| 2008/0192887 A1 | 8/2008 | Weese et al. |
| 2008/0215231 A1 | 9/2008 | Breed |
| 2008/0232545 A1 | 9/2008 | Wu et al. |
| 2008/0240502 A1 | 10/2008 | Freedman et al. |
| 2008/0240507 A1 | 10/2008 | Niwa et al. |
| 2008/0242980 A1 | 10/2008 | Lees et al. |
| 2008/0273760 A1 | 11/2008 | Metcalfe et al. |
| 2008/0273773 A1 | 11/2008 | Ernst et al. |
| 2008/0285886 A1 | 11/2008 | Allen |
| 2008/0287772 A1 | 11/2008 | Declerck et al. |
| 2008/0292146 A1 | 11/2008 | Breed et al. |
| 2008/0304706 A1 | 12/2008 | Akisada et al. |
| 2009/0010380 A1 | 1/2009 | Gotoh |
| 2009/0028409 A1 | 1/2009 | Tsukagoshi et al. |
| 2009/0060119 A1 | 3/2009 | Jupiter et al. |
| 2009/0080697 A1 | 3/2009 | Kishikawa et al. |
| 2009/0086884 A1 | 4/2009 | Krauss |
| 2009/0087068 A1 | 4/2009 | Sakaguchi |
| 2009/0087113 A1 | 4/2009 | Li et al. |
| 2009/0088633 A1 | 4/2009 | Meyer et al. |
| 2009/0088897 A1 | 4/2009 | Zhao et al. |
| 2009/0092284 A1 | 4/2009 | Breed et al. |
| 2009/0129545 A1 | 5/2009 | Adler et al. |
| 2009/0154775 A1 | 6/2009 | Lea et al. |
| 2009/0154793 A1 | 6/2009 | Shin et al. |
| 2009/0161815 A1 | 6/2009 | Grass et al. |
| 2009/0168949 A1 | 7/2009 | Bendahan et al. |
| 2009/0196397 A1 | 8/2009 | Bertozzi et al. |
| 2009/0202109 A1 | 8/2009 | Clar et al. |
| 2009/0202153 A1 | 8/2009 | Cortopassi et al. |
| 2009/0207246 A1 | 8/2009 | Inami et al. |
| 2009/0213989 A1 | 8/2009 | Harding |
| 2009/0220129 A1 | 9/2009 | Oaknin et al. |
| 2009/0252378 A1 | 10/2009 | Boese |
| 2009/0262974 A1 | 10/2009 | Lithopoulos |
| 2009/0268948 A1 | 10/2009 | Zhang et al. |
| 2009/0274352 A1 | 11/2009 | Chang et al. |
| 2009/0278684 A1 | 11/2009 | Petricoin |
| 2009/0279749 A1 | 11/2009 | Irving et al. |
| 2009/0279785 A1 | 11/2009 | Wredenhagen |
| 2009/0281415 A1 | 11/2009 | Cupps et al. |
| 2009/0283676 A1 | 11/2009 | Skoglund |
| 2009/0296998 A1 | 12/2009 | Fox et al. |
| 2009/0297000 A1 | 12/2009 | Shahaf et al. |
| 2009/0297061 A1 | 12/2009 | Mareachen et al. |

(56) References Cited

U.S. PATENT DOCUMENTS

| | | |
|---|---|---|
| 2009/0310835 A1 | 12/2009 | Kaus et al. |
| 2009/0323889 A1 | 12/2009 | Harding et al. |
| 2010/0008555 A1 | 1/2010 | Trumer et al. |
| 2010/0016712 A1 | 1/2010 | Bartal et al. |
| 2010/0027857 A1 | 2/2010 | Wang |
| 2010/0040279 A1 | 2/2010 | Yoon et al. |
| 2010/0054397 A1 | 3/2010 | Thieberger et al. |
| 2010/0067647 A1 | 3/2010 | Bani-Hashemi et al. |
| 2010/0074532 A1 | 3/2010 | Gordon et al. |
| 2010/0091146 A1 | 4/2010 | Rodriguez et al. |
| 2010/0092073 A1 | 4/2010 | Prokhorov |
| 2010/0100275 A1 | 4/2010 | Mian et al. |
| 2010/0104164 A1 | 4/2010 | Bartal et al. |
| 2010/0104166 A1 | 4/2010 | Hall et al. |
| 2010/0104174 A1 | 4/2010 | Rohlf et al. |
| 2010/0119033 A1 | 5/2010 | Li et al. |
| 2010/0158189 A1 | 6/2010 | Yoshida |
| 2010/0172560 A1 | 7/2010 | Kimmlingen et al. |
| 2010/0177968 A1 | 7/2010 | Fry et al. |
| 2010/0194773 A1 | 8/2010 | Pan et al. |
| 2010/0239133 A1 | 9/2010 | Schmitt et al. |
| 2010/0239142 A1 | 9/2010 | Dannels et al. |
| 2010/0239153 A1 | 9/2010 | Kuduvalli et al. |
| 2010/0246778 A1 | 9/2010 | Heigl et al. |
| 2010/0254595 A1 | 10/2010 | Miyamoto |
| 2010/0259609 A1 | 10/2010 | Takahashi |
| 2010/0272318 A1 | 10/2010 | Cabiri et al. |
| 2010/0274123 A1 | 10/2010 | Voth |
| 2010/0274478 A1 | 10/2010 | Takahashi |
| 2010/0284592 A1 | 11/2010 | Arnon et al. |
| 2010/0290698 A1 | 11/2010 | Freedman et al. |
| 2010/0310116 A1 | 12/2010 | Sasakawa |
| 2010/0316252 A1 | 12/2010 | Burgoa et al. |
| 2011/0019892 A1 | 1/2011 | Rahn et al. |
| 2011/0026799 A1 | 2/2011 | Nehrke et al. |
| 2011/0028183 A1 | 2/2011 | Yun |
| 2011/0032337 A1 | 2/2011 | Rodríguez et al. |
| 2011/0044504 A1 | 2/2011 | Oi et al. |
| 2011/0049384 A1 | 3/2011 | Yared et al. |
| 2011/0052042 A1 | 3/2011 | Ben |
| 2011/0060211 A1 | 3/2011 | Lorenzo et al. |
| 2011/0064191 A1 | 3/2011 | Toth et al. |
| 2011/0064269 A1 | 3/2011 | Pai et al. |
| 2011/0081071 A1 | 4/2011 | Benson et al. |
| 2011/0096182 A1 | 4/2011 | Cohen et al. |
| 2011/0096954 A1 | 4/2011 | Dahl |
| 2011/0097014 A1 | 4/2011 | Lin |
| 2011/0102427 A1 | 5/2011 | Mashitani et al. |
| 2011/0103651 A1 | 5/2011 | Nowak et al. |
| 2011/0103680 A1 | 5/2011 | Mashitani et al. |
| 2011/0103681 A1 | 5/2011 | Kelly |
| 2011/0110557 A1 | 5/2011 | Clark et al. |
| 2011/0110576 A1 | 5/2011 | Kreeger et al. |
| 2011/0112398 A1 | 5/2011 | Zarkh et al. |
| 2011/0129055 A1 | 6/2011 | Neuser et al. |
| 2011/0142337 A1 | 6/2011 | Deonarine et al. |
| 2011/0149089 A1 | 6/2011 | Yang |
| 2011/0152684 A1 | 6/2011 | Altmann et al. |
| 2011/0158508 A1 | 6/2011 | Shpunt et al. |
| 2011/0164732 A1 | 7/2011 | Bertozzi et al. |
| 2011/0176713 A1 | 7/2011 | Asaka |
| 2011/0188737 A1 | 8/2011 | Prokhorov et al. |
| 2011/0191023 A1 | 8/2011 | Engstrom |
| 2011/0243409 A1 | 10/2011 | Naimi et al. |
| 2011/0255665 A1 | 10/2011 | Breedveld |
| 2011/0261193 A1 | 10/2011 | Agurok et al. |
| 2011/0312374 A1 | 12/2011 | Chen et al. |
| 2011/0313479 A1 | 12/2011 | Rubin |
| 2012/0014500 A1 | 1/2012 | Flohr et al. |
| 2012/0020536 A1 | 1/2012 | Moehrle |
| 2012/0020547 A1 | 1/2012 | Zhao et al. |
| 2012/0027176 A1 | 2/2012 | Heid |
| 2012/0045111 A1 | 2/2012 | Palma et al. |
| 2012/0057775 A1 | 3/2012 | Suzuki et al. |
| 2012/0057779 A1 | 3/2012 | El |
| 2012/0063665 A1 | 3/2012 | Wang et al. |
| 2012/0063672 A1 | 3/2012 | Gordon et al. |
| 2012/0083982 A1 | 4/2012 | Bonefas et al. |
| 2012/0087546 A1 | 4/2012 | Focke et al. |
| 2012/0087559 A1 | 4/2012 | Hellier et al. |
| 2012/0106796 A1 | 5/2012 | Jones et al. |
| 2012/0123256 A1 | 5/2012 | Razansky et al. |
| 2012/0141046 A1 | 6/2012 | Chen et al. |
| 2012/0148147 A1 | 6/2012 | Ogata et al. |
| 2012/0155715 A1 | 6/2012 | Buscema |
| 2012/0273684 A1* | 11/2012 | Akery .................. 250/360.1 |
| 2013/0235971 A1* | 9/2013 | Oreper et al. ............ 378/19 |

\* cited by examiner

3D MAPPING WITH TWO ORTHOGONAL IMAGING VIEWS

TECHNICAL FIELD

This specification generally relates to imaging systems, and specifically to generating location and size measurements for small scattered objects in a large medium.

BACKGROUND

When analyzing the distribution pattern of an explosion, the explosive under investigation may be surrounded by mediums (e.g., fiber bundles) that are adapted to capture fissile fragments within a test arena. The explosion causes fissile fragments (e.g., metal objects) to be embedded inside the fiber bundles. These fiber bundles are then dismantled by hand to map the locations of fissile fragments from the explosion. However, dismantling the fiber bundles by hand is a costly and labor intensive process.

SUMMARY

According to an innovative aspect of the subject matter described in this specification, a radiation system is used to map the location of embedded objects inside a medium without destroying the absorbing media. To determine the location of the objects, the medium may be scanned with radiation (e.g., X-rays or neutrons). However, using one radiation source and one line of detectors may not provide the data necessary to locate the coordinates of each object. Accordingly, two orthogonal radiation sources and corresponding detectors may be used to determine the location of objects embedded in the mediums. The data collected by the detectors can then be used to determine the angular location of the objects for each source. The two angular locations can be used to determine the Cartesian coordinates that describe the absolute location of each of the objects in the medium.

In general, one innovative aspect of the subject matter described in this specification may be embodied in systems that include a first radiation source; a first detector; a second radiation source oriented substantially orthogonally to the first radiation source; a second detector located substantially orthogonally to the first detector; and one or more computers and one or more storage devices. The first detector is configured to detect first radiation from the first radiation source during irradiation of a medium. The medium includes one or more embedded objects. The second detector is configured to detect second radiation from the second radiation source during irradiation of the medium. The one or more computers and the one or more storage devices store instructions that are operable and when executed by the one or more computers cause the one or more computers to perform the operations that include receiving first data from the first detector, the first data associated with the detected first radiation; receiving second data from the second detector, the second data associated with the detected second radiation; and determining a location of at least one of the one or more embedded objects based on the detected first data and the detected second data, the location being relative to the medium.

These and other embodiments can each optionally include one or more of the following features. The location includes a first coordinate and a second coordinate, the first coordinate being associated with a first dimension and the second coordinate being associated with a second dimension, the first dimension and the second dimension being substantially orthogonal. The location includes a first coordinate and a second coordinate, the first coordinate and the second coordinate being Cartesian coordinates. The first radiation source and the second radiation source produce X-rays. The first radiation source and the second radiation source are neutron sources. The operation of receiving first data from the first detector, the first data associated with the detected first radiation includes determining, based on the first data, a first angle associated with at least one of the one or more embedded objects.

The operation of receiving second data from the second detector, the second data associated with the second radiation includes determining, based on the second data, a second angle associated with at least one of the one or more embedded objects. The operation of determining a location of at least one of the one or more embedded objects based on the received first data and the received second data, the location being relative to the medium includes determining a distance between the first radiation source and the second radiation source; determining a first coordinate based on a first ratio of (i) the distance between the first radiation source and the second radiation source and (ii) a first function of the first angle and the second angle; and determining a second coordinate based on a second ratio of (i) the distance between the first radiation source and the second radiation source and a second function of the first angle and (ii) the first function of the first angle and the second angle.

The operations further include determining a first magnification error based upon (i) a distance between the first detector and the first radiation source, (ii) a distance between the first detector and the at least one of the one or more embedded objects, and (iii) a size of the at least one of the one or more embedded objects; and determining a second magnification error based upon (i) a distance between the second detector and the second radiation source, (ii) a distance between the second detector and the at least one of the one or more embedded objects, and (iii) a size of the at least one of the one or more embedded objects. A direction of emission of the radiation from the first radiation source is substantially orthogonal to a direction of emission of the radiation from the second radiation source.

In general, another innovative aspect of the subject matter described in this specification may be embodied in methods that include the actions of receiving first data from a first detector, wherein the first detector detects radiation from a first radiation source during irradiation of a medium, wherein the medium includes one or more embedded objects; receiving second data from a second detector oriented substantially orthogonally to the first detector, wherein the second detector receives radiation from a second radiation source located substantially orthogonally to the first radiation source during irradiation of the medium; and determining a location of at least one of the one or more embedded objects based on the received first data and the received second data, the location being relative to the medium.

These and other embodiments can each optionally include one or more of the following features. The location comprises a first coordinate and a second coordinate, the first coordinate being associated with a first dimension and the second coordinate being associated with a second dimension, the first dimension and the second dimension being substantially orthogonal. The location comprises a first coordinate and a second coordinate, the first coordinate and the second coordinate being Cartesian coordinates. The first radiation source and the second radiation source produce X-rays. The first radiation source and the second radiation source are neutron sources. The action of receiving first data from the first detector, the first data associated with the received first radiation includes determining, based on the first data, a first angle associated with the at least one of the one or more embedded objects.

The action of receiving second data from the second detector, the second data associated with the second radiation includes determining, based on the second data, a second angle associated with the at least one of the one or more embedded objects. The action of determining a location of at least one of the one or more embedded objects based on the received first data and the received second data, the location being relative to the medium includes determining a distance between the first radiation source and the second radiation source; determining a first coordinate based on a first ratio of (i) the distance between the first radiation source and the second radiation source and (ii) a first function of the first angle and the second angle; and determining a second coordinate based on a second ratio of (i) the distance between the first radiation source and the second radiation source and a second function of the first angle and (ii) the first function of the first angle and the second angle.

The actions further include determining a first magnification error based upon (i) a distance between the first detector and the first radiation source, (ii) a distance between the first detector and the at least one of the one or more embedded objects, and (iii) a size of the at least one of the one or more embedded objects; and determining a second magnification error based upon (i) a distance between the second detector and the second radiation source, (ii) a distance between the second detector and the at least one of the one or more embedded objects, and (iii) a size of the at least one of the one or more embedded objects. A direction of emission of the radiation from the first radiation source is substantially orthogonal to a direction of emission of the radiation from the second radiation source.

Particular embodiments of the subject matter described in this specification can be implemented so as to realize one or more of the following advantages. The absolute location of objects embedded in a medium can be determined. The location of imperfections in a medium can be determined. Voids within a medium can be detected.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
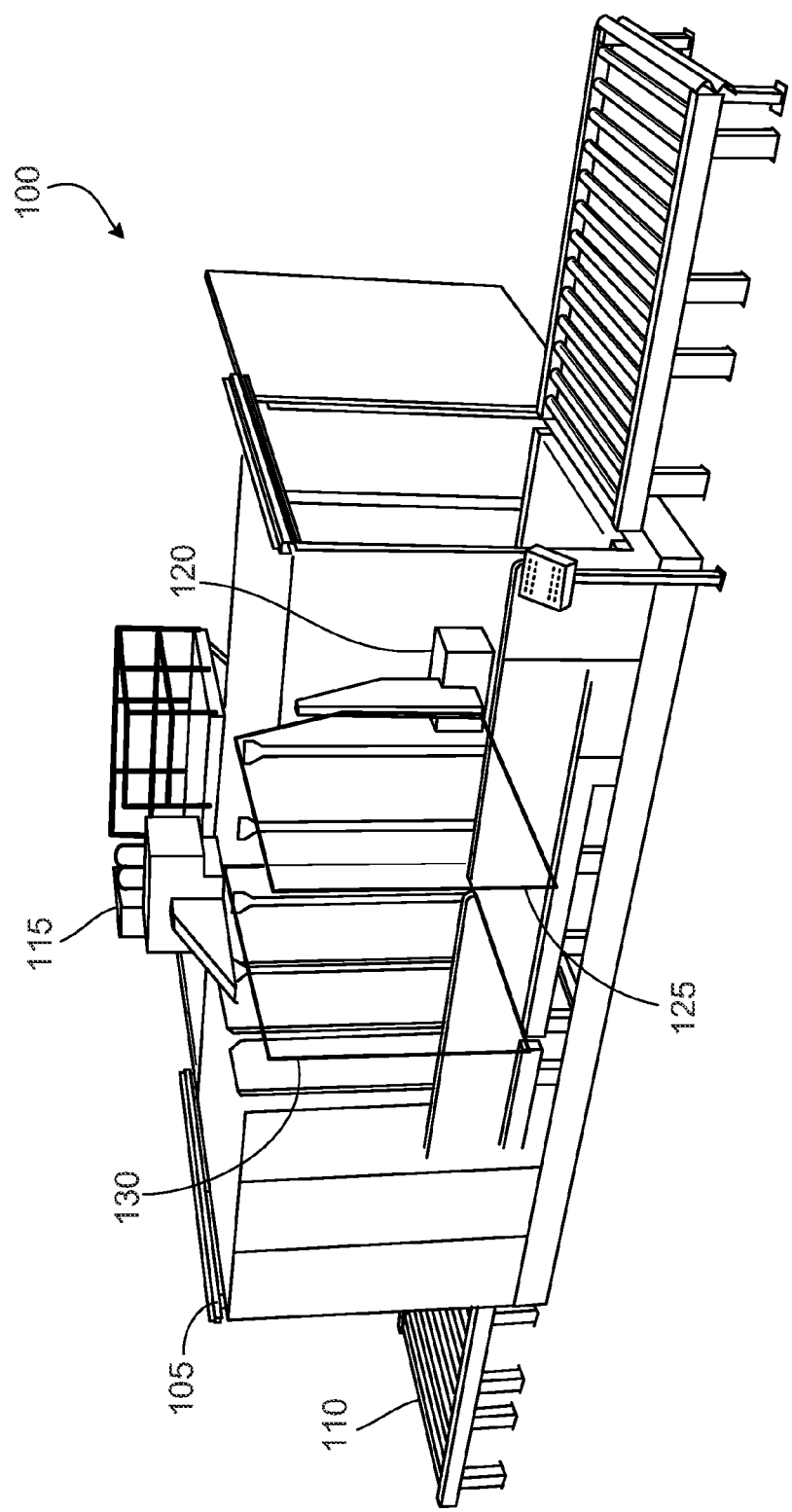
FIG. 1 is an example system for mapping the location of an object within a medium in three dimensions.

FIG. 1 shows an example imaging system 100. The imaging system 100 irradiates a medium to determine locations of objected embedded in the medium. As described herein, a medium may be a fiber bundle having metal objects embedded within it as a result of an explosion. A fiber bundle may be, for example, made from cellulose ($C_6H_{10}O_5$) or any other suitable material, and may be, for example, a 4'×4'×8' block or have any other suitable dimensions. The metal objects may be, for example, steel, brass, aluminum, titanium, copper, and/or tungsten fragments ranging from approximately 0.2 g to approximately 1 kg.

The system 100 includes a transport mechanism 110 that transports the medium through an enclosure 105. The radiation sources 115 and 120 are located substantially orthogonally to each other and are positioned to scan (e.g., irradiate) a medium that is passing through the enclosure 105 along the transport mechanism 110. As described herein, substantially orthogonal means about 90° with respect to each other.

During operation of the imaging system 100, a medium is placed on the transport mechanism 110. An operator activates the transport mechanism 110 to move the medium through the enclosure 105. As the medium passes through the enclosure 105, the radiation sources 115 and 120 produce radiation in the direction of the medium passing along the transport mechanism 110. The radiation from the first radiation source 115 is detected by the line of detectors 125. Some of the radiation generated by the first radiation source 115 is absorbed by the medium and some of the radiation is absorbed by the first detector 125. Similarly, some of the radiation generated from the second radiation source 120 is absorbed by the medium and some of the radiation is absorbed by the second detector 130. As the transport mechanism 110 continues to advance the medium, a different cross section of the medium is exposed to the radiation. Once the object has completely passed through the path of the radiation sources 115 and 120, the detectors 125 and 130 have two sets of data that are related to the radiation absorbed by the object, but from two orthogonal viewpoints.

In some implementations, the medium being irradiated is a fiber bundle. Prior to irradiating the fiber bundle, the fiber absorbs small objects that are typically metal objects generated by an explosion. In some implementations, the medium may be composed of any other suitable material as long as the objects to be detected absorb radiation at a different level than the medium. For example, the medium may be a finished manufactured product with unknown defects. In this instance, the system 100 would identify the location of the defects. As another example, the medium may be a metal shell with explosive material inside the metal shell. The explosive material may not fill the entire area inside the metal shell. The system 100 would identify the location of air pockets within the explosive material.

In some implementations, the first radiation source 115 and the second radiation source 120 generate X-rays and the first detector 125 and the second detector 130 detect X-rays. In other implementations, the radiation sources 115 and 120 are neutron sources and the detectors 125 and 130 are neutron detectors. In some implementations, the detectors 125 and 130 are composed of a line of detectors. For example, two lines of detectors may be placed adjacently to produce an L-shaped folded line of detectors. In other implementations, multiple detectors may be placed in an arc such that the distance between a radiation source and any detector is constant.

In some implementations, the transport mechanism 110 is a conveyor belt. For example, the medium is placed on a belt and advances through the irradiation path of the radiation sources 115 and 120. In other implementations, the transport mechanism 110 is an apparatus where the medium is kept stationary while the radiation source 115 and 120 and the detectors 125 and 130 move along a path defined by rails and irradiate a different cross section of the medium. In other implementations, the transport mechanism 110 is an apparatus where the medium is kept stationary while the radiation source 115 and 120 and the detectors 125 and 130 move along the detectors' own wheels and irradiate a different cross section of the medium. In other implementations, the transport mechanism 110 is an apparatus where the medium is kept stationary while the radiation source 115 and 120 and the detectors 125 and 130 move on their own transport system, such as tractors with trails, and irradiate a different cross section of the medium. In other implementations, the transport mechanism 110 is an apparatus where the medium is pulled along a platen that is tugged by a pulling system while the radiation source 115 and 120 and the detectors 125 and 130 are kept stationary.

As the medium advances, or is advanced, along the transport mechanism 110, a cross section of the medium receives direct radiation from the radiation sources 115 and 120. Radiation generated from the first radiation source 115 is projected in one direction, and radiation generated from the second radiation source 120 is projected in a direction that is about orthogonal to the direction of projection of the first radiation source 115. The radiation from both radiation sources 115 and 120 are directed radially at a particular angle that is dictated by the radiation source. As the radiation encounters the cross section of the medium, some of the radiation is absorbed by the embedded objects within the medium if those objects are in the particular cross section under direct radiation. The radiation not absorbed by the object or the embedded particles will travel to the detectors. The detectors record the location and intensity of the received radiation.

The location data recorded by one line of detectors, for example the first detector 125, contains two coordinates ($\Theta 1$, z). The coordinates may be based upon a cylindrical coordinate system with an angle ($\Theta 1$) and a longitudinal direction (z) that is perpendicular to the measured angle. The longitudinal direction is parallel with the direction of motion. The location data recorded by the other line of detectors, for example, the second detector 130, also may be based on a cylindrical coordinate system that contains two coordinates ($\Theta 2$, z).

As noted above, in some implementations, the detectors 125 and 130 are arranged in an arch. In this instance the distance between a radiation source and different point along a detector is constant. In other implementations, the detectors 125 and 130 may be arranged in a straight line or in an L-shape. Whether the detectors 125 and 130 are arranged in a straight line, an arch, or an L-shape, the imaging system 100 can produce the angle measurement information. Where the detectors 125 and 130 are arranged in an L-shape, the imaging system 100 can use a table that shows the angular position of each detector. The table can include the distance between each detector and the radiation source.

Figure 4:
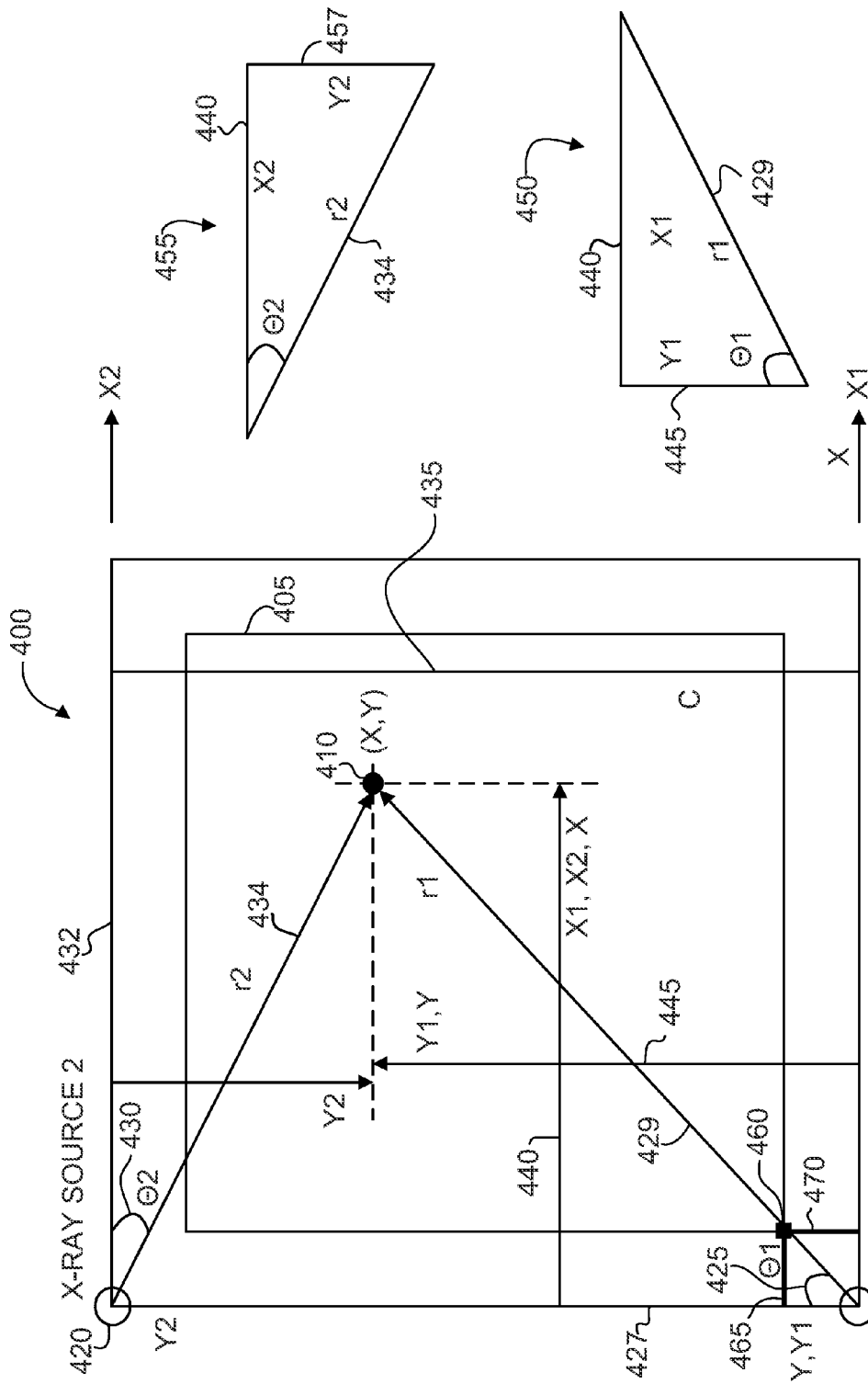
FIG. 4 shows the coordinate transformation geometry for an embedded object.

As illustrated in FIG. 4, the measured angles 425 and 430 are polar angles formed between the fixed lines 427 and 432 and the lines formed by the radiation beam 429 and 434, respectively. The fixed line 427 defines the direction of the second Cartesian coordinate. The fixed line 427 for the first radiation source 115 is perpendicular to the transport mechanism 110. The fixed line 432 defines the direction of the first Cartesian coordinate. The fixed line 432 for the second radiation source 120 is located perpendicular to the transport mechanism 110.

Figure 2A:
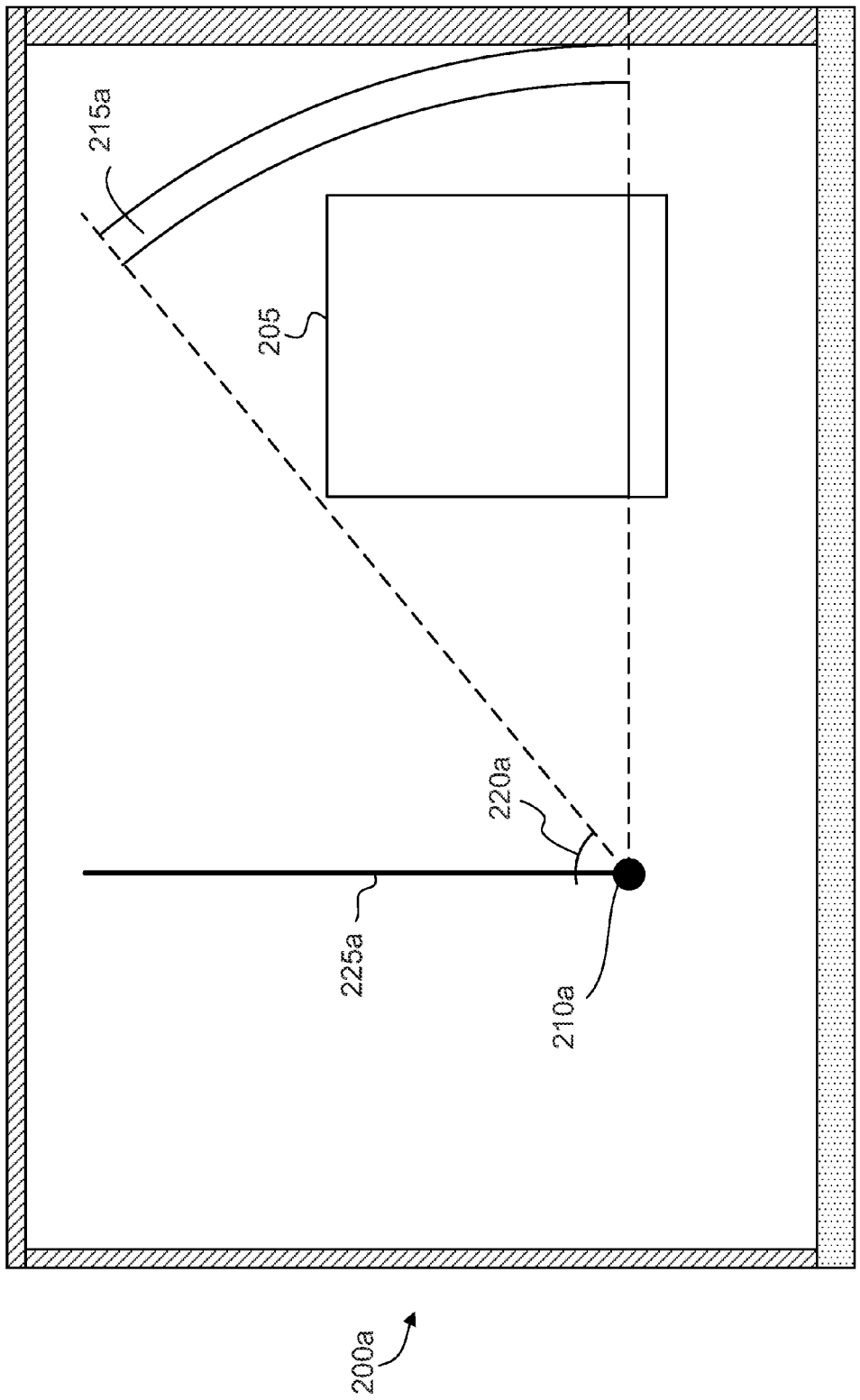
FIG. 2A shows a typical cross section of a medium being irradiated by a first radiation source.

FIG. 2A shows a typical cross section of the irradiated medium and the location of one of the radiation sources. Cross section 200a shows a typical cross section of irradiated medium 205 and the location of the first radiation source 210a. The first radiation source 210a generates radiation that is absorbed by the medium 205. The radiation that is not absorbed by the medium 205 is virtually all absorbed by the detector 215a.

In cross section 200a, the medium 205 is square. In some implementations, the medium 205 is rectangular. Although the medium 205 is not required to be square or rectangular, a medium with a section that contains four sides and four right angles is selected for practical implementation. The objects embedded in the medium to be scanned can have any shape. Furthermore, a reference marker in the medium 205 is typically used. A reference marker is an intentionally embedded object within the medium. The reference marker absorbs radiation at a different rate than the medium. The reference marker provides a user defined origin for determining relative locations of the objects within the medium with respect to the marker. In some implementations, the enclosure may not be square or rectangular. For example, the enclosure may be triangular or circular. These types of enclosures may be used to accommodate different types and shapes of mediums. The transport mechanism (not shown) advances the medium 205 or the first radiation source 210a and the detector 215a. As illustrated in FIG. 2A, the medium 205 can either be traveling into the page or out of the page.

The first radiation source 210a projects radiation in the direction of the medium 205. The radiation source projects radiation throughout an angular range 220a. The angular range 220a provides a wide enough range to irradiate the entire cross section of the medium 205 either at substantially the same time or as individual radiation beams that are projected individually over a period of time. The angular range 220a can be adjusted depending on the size and location of the medium 205. For example, if the medium 205 has a square cross section, then the angular range 220a of the side radiation source 210a can be decreased so that only the object 205 is irradiated over the square cross section and not extra portions of the enclosure.

The radiation from the first radiation source 210a is partly absorbed by the medium 205 and partly by the detector 215a. In cross section 200a, the detector 215a is an arc shaped detector and therefore the distance between the detector 215a and the first radiation source 210a remains constant for each location on the detector 215a for each cross section of medium 205. In some implementations, the detector 215a requires minimum clearances between the medium 205 and the first detector 215a.

Figure 2B:
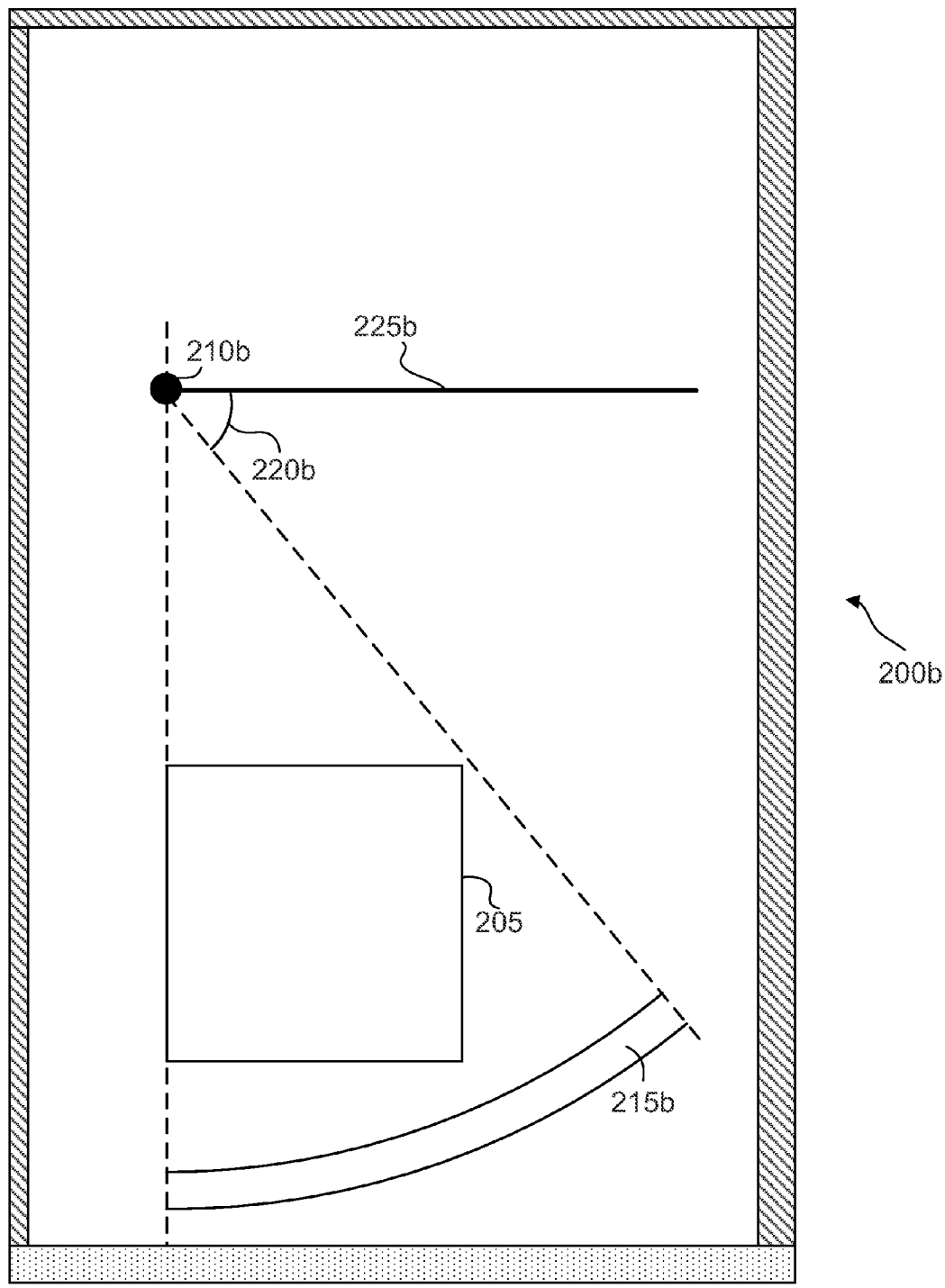
FIG. 2B shows a typical cross section of a medium being irradiated by a second radiation source that is about orthogonal to the first radiation source.

FIG. 2B shows a typical cross section of the irradiated medium and the location of another of the radiation sources. Cross section 200b shows a similar cross section to 200a, but in cross section 200b, the second radiation source 210b is positioned above the medium 205. Cross sections 200a and 200b may not represent two cross sections of different enclosures, but rather, the same cross section of an enclosure. Cross section 200a shows the medium 205 with the first radiation source 210a and the first detector 215a. Cross section 200b shows the medium 205 with the second radiation source 210b and the second detector 215b. A complete cross section of the enclosure would show both radiation sources 210a and 210b and both detectors 215a and 215b since they are all used for accurate imaging of the medium 205.

Similar to cross section 200a, cross section 200b contains a radiation source 210b that can direct radiation for a particular angle range 220b. The detector 215b is an arc shaped line of detector. In some implementations, the second detector 215b requires minimum clearances between the medium 205 and the second detector 215b.

The reference lines used to measure the angle of radiation on the detectors 215a and 215b is shown, for example, by reference lines 225a and 225b. Reference line 225a denotes the base line used to measure the angle of the radiation detected by the first detector 215a and generated by the first radiation source 210a. Reference line 225b denotes the base line used to measure the angle of the radiation detected by the second detector 215b and generated by the second radiation source 210b.

Figure 3:
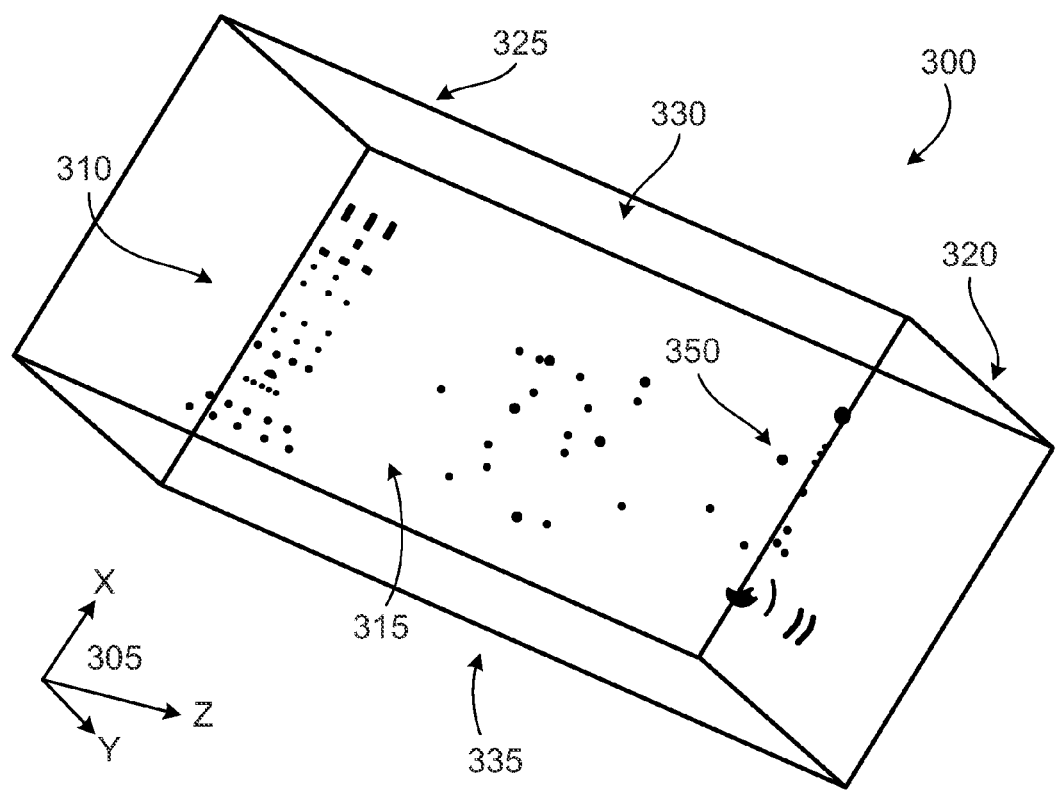
FIG. 3 shows a three-dimensional view of a medium with embedded objects.

FIG. 3 shows a three dimensional view of a medium 300. Medium 300 shows objects 350 distributed throughout the medium 300. Each of the objects 350 embedded in the medium 300 is located at a particular Cartesian coordinate with respect to an origin. The direction of each Cartesian coordinate is indicated by directions 305. The system can determine a Cartesian coordinate of each embedded object.

The directions 305 indicate an x, y, and z direction and all three are orthogonal to each other. Medium face 310 is in the negative (x, y) plane. Medium face 315 is in the negative (x, z) plane. Medium face 320 is in the positive (x, y) plane. Medium face 325 is in the positive (x, z) plane. Medium face 330 is in the positive (y, z) plane. Medium face 335 is in the negative (y, z) plane.

FIG. 4 shows a cross section of the medium and the measurements associated with an object embedded in the medium. The cross section 400 includes a cross section of the irradiated medium 405 and an embedded object 410. The object 410 absorbs radiation differently than the medium 405. The first radiation source 415 and the second source 420 generate radiation that is absorbed by the detectors. The detectors record data that indicates angle Θ1 425 for the first radiation source 415 and angle Θ2 430 for the second radiation source 420. The distance between the first radiation source 415 and the second radiation source 420 is indicated by measurement C 435. Using the angles Θ1 425 and Θ2 430, the system can determine Cartesian distances x 440 and y 445. Cartesian distance x 440 indicates the perpendicular distance from the line connecting the radiation sources 415 and 420. Cartesian distance y 445 indicates the distance perpendicular to Cartesian distance x 440 and originating from a line intersecting the first radiation source 415. In some implementations, Cartesian distance y 445 originates from a line intersecting the first radiation source 420.

Cartesian distances x 440 and y 445 identify the location of the embedded object 410 within the medium 405. As discussed above, when a single radiation source is used, the angle identifies a range along the edge of the angle where an embedded object may be located. By using two radiation sources, the absolute location of the embedded particle can be determined.

Right triangle 450 includes sides that equal Cartesian distances x 440 and y 445 and an angle that equals angle Θ1 425. Therefore, equation (1) describes the relationship between the Cartesian distances x 440 and y 445 and angle Θ1 425.

$$\tan(\text{angle } \Theta1\ 425) = \frac{\text{cartesian distance } x\ 440}{\text{cartesian distance } y\ 445} \quad (1)$$

Right triangle 455 includes a side that equals Cartesian distance 440 and an angle that equals angle Θ2 430. Additionally, right triangle 455 includes a side 457 that is a function of distance C 435 and Cartesian distance y 445. Therefore, equation (2) describes the relationship between Cartesian distances x 440 and y 445, distance C 435, and angle Θ1 430.

$$\tan(\text{angle } \Theta2\ 430) = \frac{(\text{distance } C\ 435) - (\text{cartesian distance } y\ 445)}{\text{cartesian distance } x\ 440} \quad (2)$$

In some implementations where Cartesian distance y 445 is measured from a line intersecting the second radiation source 420. Equations (1) and (2) remain the same except in equation (1), Cartesian distance y 445 is replaced with (distance C 435)–(Cartesian distance y 445). Similarly, in equation (2), (distance C 435)–(Cartesian distance y 445) is replaced with distance y 445.

Algebraic manipulation of equations (1) and (2) yields equations for Cartesian distances x 440 and y 445 given by equations (3) and (4).

$$\text{cartesian distance } x\ 440 = \frac{\text{distance } C\ 435}{\tan(\text{angle } \Theta2\ 430) + \cot(\text{angle } \Theta1\ 425)} \quad (3)$$

$$\text{cartesian distance } y\ 455 = \frac{(\text{distance } C\ 435) * (\cot(\text{angle } \Theta1\ 425))}{\tan(\text{angle } \Theta2\ 430) + \cot(\text{angle } \Theta1\ 425)} \quad (4)$$

Equations (3) and (4) can be applied to each embedded object to determine the location within the medium 405. When combined with the data describing the longitudinal location, each embedded object can be uniquely identified by its location using the derived Cartesian distances.

Figure 5:
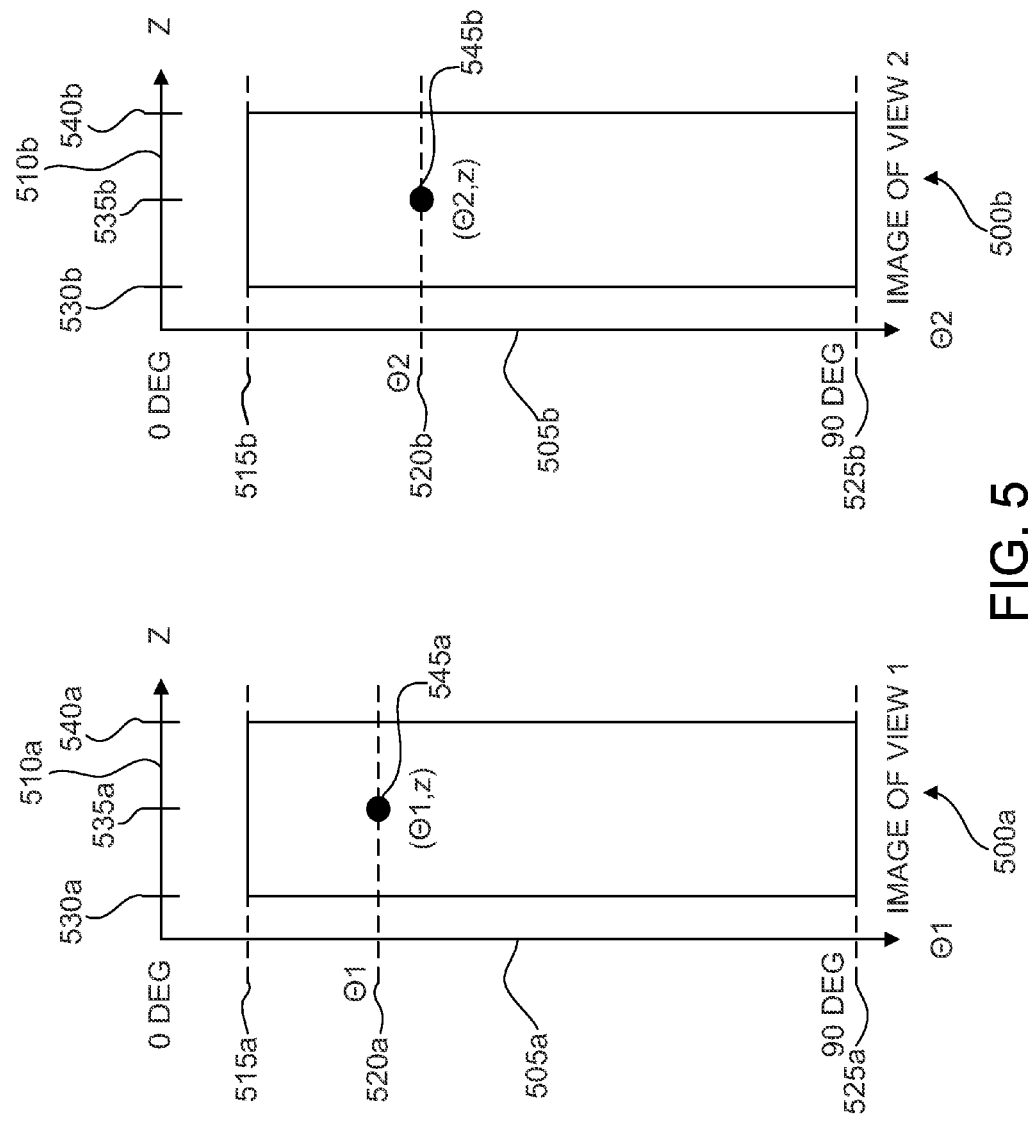
FIG. 5 shows locations of an object detected by a first radiation detector and a second radiation detector.

FIG. 5 shows locations of an object detected by a first detector and a second detector. Graph 500a shows the location of an object within a medium as detected by a first detector. Graph 500b shows the location of the object within a medium as detected by a second detector.

Graph 500a is composed of an angle axis 505a and a longitudinal axis 510a. In Graph 500a, angle axis 505a is marked with three angular measurements. First, the angular measurement 515a is the angle at which the first detector detected radiation that had been altered by the medium. Between zero degrees and angular measurement 515a, the first detector did not detect radiation that had been altered by the medium. In some implementations, the first detector cannot detect radiation between zero degrees and a particular angle. For example, the first detector may not be able to detect radiation between zero degrees and fifteen degrees. Thus, zero degrees to fifteen degrees would not be in the field of view of the first detector. Second, the angular measurement 520a is the angle at which the first detector detected radiation that had been altered by an objected embedded in the medium. Third, the angular measurement 525a is the angle at which the first detector again did not detect radiation that had been altered by the medium.

The longitudinal axis 510a is marked by three measurements. First, the measurement 530a is the location at which the medium first begins to pass through the radiation generated by the first radiation source. Second, the measurement 535*a* is the location at which the first detector detected radiation that had been altered by an objected embedded in the medium. Third, the measurement 540*a* is the location at which the medium last passed through the radiation generated by the first radiation source. Coordinate 545*a* indicates the location of the embedded object as measured by the first detector.

Graph 500*a* summarizes the output of the first detector. The graph 500*a* displays the ranges of angular measurements and longitudinal measurements where the medium passes through the radiation produced by the first radiation source. If there were multiple objects embedded in the medium, then there would be multiple coordinates on the graph 500*a* indicating the location of the embedded objects.

Similarly, graph 500*b* summarizes the output of the second detector. The graph displays the ranges of angular measurements and longitudinal measurements where the medium passes through the radiation produced by the second radiation source. For example, graph 500*b* shows angular measurements 515*b* and 525*b* on angular axis 505*b* as the range of angles where the medium altered radiation produced by the second radiation source. Angular measurement 520*b* on the angular axis 505*b* represents the location where the second detector detected radiation that had been altered by the object embedded in the medium. Longitudinal measurements 530*b* and 540*b* on the longitudinal axis 510*b* as the range of longitudinal measurements where the medium altered radiation produced by the second radiation source. Longitudinal measurement 535*b* on the longitudinal axis 510*b* represents the location where the radiation had been altered by the object embedded in the medium. Coordinate 545*b* indicates the location of the embedded object measured by the second detector.

Figure 6:
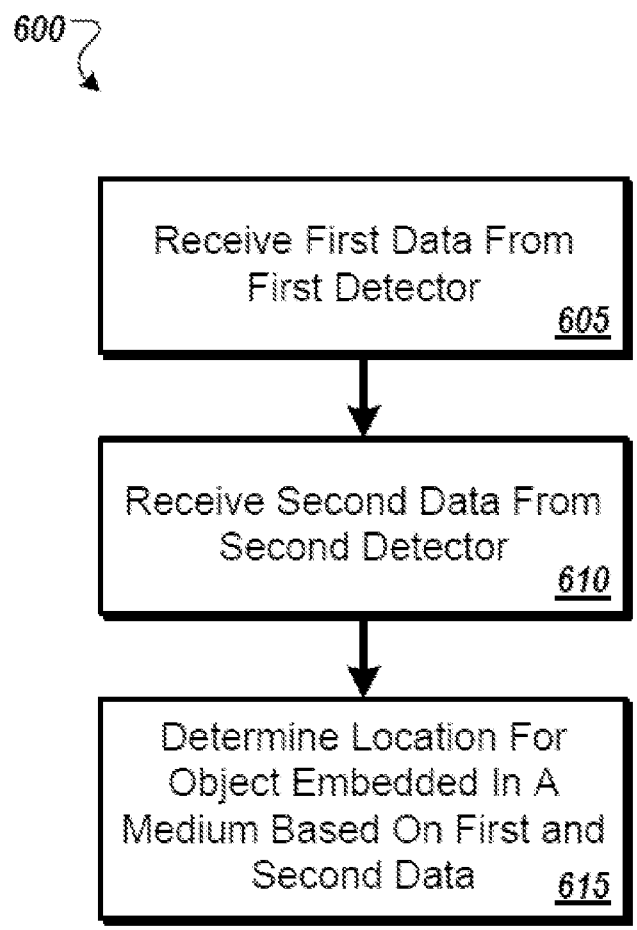
FIG. 6 is an example method for mapping an object in three dimensions.

FIG. 6 shows an example of a process 600 for computing coordinates of an embedded object, for example, object 410 in FIG. 4, using radiation. The process 600 collects data received by a first detector and a second detector during irradiation of a medium. In some implementations, the medium is a fiber bundle that has many embedded objects that were embedded from an explosion that detonated near the medium. The process 600 processes the received data and computes coordinates that identify the location of each embedded object in three dimensions. The process 600 will be described as being performed by an imaging system, for example, the system 100 as shown in FIG. 1.

The system receives first data from a first detector (605). The first detector absorbs radiation that is generated by a first radiation source, for example, radiation source 415 as shown in FIG. 4. The first radiation source is located in a position where it can expose a cross section of the medium, for example, medium 405 as shown in FIG. 4, to radiation. Some of the radiation is absorbed by the medium. Various levels of absorption occur depending on whether the radiation is absorbed by the medium or an object, for example, object 410 as shown in FIG. 4, embedded in the medium. The first detector absorbs the radiation that has passed through or been attenuated by the medium and the embedded objects. The system uses the data gathered by the first detector to determine two measurements associated with each object. The first measurement is a polar angle, for example, angle 425 as shown in FIG. 4, that measures the angle created between a reference line, for example, fixed line 427 as shown in FIG. 4, and a line passing through the object and the first radiation source, for example, radiation line 429 as shown in FIG. 4.

The second measurement is a measurement along a longitudinal axis. The second measurement represents the location of the cross section of the medium where the object is located.

When combined, the first and the second measurements are similar to cylindrical coordinates. Cylindrical coordinates typically contain a radius, an angle, and a longitudinal distance. The system determines the angle and the longitudinal distance. The radius is constant for each location on the first detector. For example, if a radiation photon is directed at a particular angle towards an embedded object that is a particular distance away and the photon is absorbed by the object, the first detector will detect attenuated radiation at the location of the particular angle on the detector. If a radiation photon is directed at the particular angle towards an embedded object that is double the particular distance away and the photon is absorbed by the object, the first detector will detect attenuated radiation at the location of the particular angle on the detector. In other words, the first detector detects the angle of the radiation produced by the first radiation source, but lacks enough information to determine the radial distance of the particle from the source.

The system receives second data from a second detector that is located about orthogonally to the first detector (610). The second detector detects radiation from a second radiation source, for example, radiation source 420 as shown in FIG. 4. The second radiation source is located about orthogonally to the first radiation source. For example, if the first radiation source is located to the side of the medium and projects radiation generally horizontally, the second radiation source would be located above the medium and project radiation generally downward. Similar to the first detector, the second detector can detect the angle, for example, angle 430 as shown in FIG. 4, of the detected radiation, but lacks enough information to determine the radial distance, for example, radiation line 434 as shown in FIG. 4, from the second source to a particular object embedded in the medium. In some implementations, the longitudinal measurement is not determined with data collected by the first and second detectors. For example, the longitudinal measurement can be determined based upon the location of the transport mechanism used to move the medium through the path of the radiation. The location of the transport mechanism can be set to zero when the first cross section of the medium is irradiated.

The system determines the first coordinate 440 and the second coordinate 445 of an embedded object based on the first angular data 425 and the second angular data 430 (615). The first data may correspond to the radiation angle 425 associated with the left vertical reference line 427 and the line 429 between the first source and the embedded object. The second data may correspond to the radiation angle 430 associated with the top horizontal reference line 432 and the line 434 between the second source and the embedded object. The first coordinate 440 corresponds to the first Cartesian distance identifying a location of the embedded object with respect to the reference point 415. For example, the first coordinate may correspond to the first Cartesian distance 440 as shown in FIG. 4. The second coordinate 445 corresponds to the second Cartesian distance identifying a location of the embedded object. For example, the second coordinate may correspond to the second Cartesian distance 445 as shown in FIG. 4.

As described above, (i) the radiation angle 425 associated with left vertical reference line 427 and the line 429 between the first source and the embedded object, (ii) the radiation angle associated with top horizontal reference line 432 and the line 434 between the second source and the embedded object, and (iii) the distance 435 between the first source and the second source, may be combined to determine the first Cartesian distance 440 and the second Cartesian distance 445.

The system determines the first Cartesian distance 440 and the second Cartesian distance 445 with respect to an origin 415. In some implementations, the origin is the radiation point of the first source, for example, the first source 415 as shown in FIG. 4. If the origin is the first source, then the system determines the first Cartesian distance 440 and second Cartesian distance 445 using Equations (5) and (6).

$$\text{first cartesian distance (440)} = \frac{\text{distance between sources (435)}}{\tan(\text{second detector angle (430)}) + \cot(\text{first detector angle (425)})} \quad (5)$$

$$\text{second cartesian distance (445)} = \frac{(\text{distance between sources (435)}) * (\cot(\text{first detector angle (425)}))}{\tan(\text{second detector angle (430)}) + \cot(\text{first detector angle (425)})} \quad (6)$$

Equations (5) and (6), along with the location of the transport mechanism, can be applied to each embedded object in the medium to uniquely identify the absolute location of each object in Cartesian coordinates. In other implementations, the user defined origin may not be one of the radiation sources, but rather a reference marker. For example, a metal cross may be placed at a corner of the medium, and the metal cross provides the user defined origin. In this case, the system calculates the first and second Cartesian distances as given in Equations (5) and (6) and adjusts the first and second Cartesian distances by additional offsets. As shown in FIG. 4, the reference marker may be placed at location 460. The system would subtract offset 465 from the first Cartesian distance 440 and subtract offset 470 from the second Cartesian distance 445. Additionally, the system would correct the longitudinal measurements based on the reference marker.

The detectors typically cannot see the actual size of the particle, just the pattern of the detected radiation. Because the radiation is coming from a point source, the "shadow" cast by an object that absorbs a portion of the radiation will be greater at the detector than the size of the object. The "shadow" will be larger as the object is located farther from the detector. The "shadow" will be closer to the object size as the object is located closer to the detector. The error in estimation of the object size can be corrected once the system determines the location of the object. The magnification error can be calculated with equation (7).

$$\text{measurement error due to magnification} = \left(\frac{(\text{source to detector distance})}{(\text{source to object distance})} - 1\right) * (\text{object size}) \quad (7)$$

A number of implementations have been described. Nevertheless, it will be understood that various modifications may be made without departing from the spirit and scope of the disclosure. Accordingly, other implementations are within the scope of the following claims.

The invention claimed is:

1. A system comprising:
    a first radiation source;
    a first detector configured to:
       detect first radiation from the first radiation source during irradiation of a medium, wherein the medium includes one or more embedded objects;
    a second radiation source oriented substantially orthogonally to the first radiation source;
    a second detector located substantially orthogonally to the first detector configured to:
       detect second radiation from the second radiation source during irradiation of the medium; and
    one or more computers and one or more storage devices storing instructions that are operable, when executed by the one or more computers, to cause the one or more computers to perform operations comprising:
       receiving first data from the first detector, the first data associated with the detected first radiation, the receiving the first data including determining, based on the first data, a first angle associated with at least one of the one or more embedded objects;
       receiving second data from the second detector, the second data associated with the detected second radiation, the receiving the second data including determining, based on the second data, a second angle associated with at least one of the one or more embedded objects; and
       determining a location of at least one of the one or more embedded objects based on the detected first data and the detected second data, the location being relative to the medium, the determining the location including:
          determining a distance between the first radiation source and the second radiation source;
          determining a first coordinate based on a first ratio of (i) the distance between the first radiation source and the second radiation source and (ii) a first function of the first angle and the second angle; and
          determining a second coordinate based on a second ratio of (i) the distance between the first radiation source and the second radiation source and a second function of the first angle and (ii) the first function of the first angle and the second angle.

2. The system of claim 1, wherein the location comprises a first coordinate and a second coordinate, the first coordinate being associated with a first dimension and the second coordinate being associated with a second dimension, the first dimension and the second dimension being substantially orthogonal.

3. The system of claim 1, wherein the location comprises a first coordinate and a second coordinate, the first coordinate and the second coordinate being Cartesian coordinates.

4. The system of claim 1, wherein the first radiation source and the second radiation source produce X-rays.

5. The system of claim 1, wherein the first radiation source and the second radiation source are neutron sources.

6. The system of claim 1, wherein the operations further comprise:
    determining a first magnification error based upon (i) a distance between the first detector and the first radiation source, (ii) a distance between the first detector and the at least one of the one or more embedded objects, and (iii) a size of the at least one of the one or more embedded objects; and
    determining a second magnification error based upon (i) a distance between the second detector and the second radiation source, (ii) a distance between the second detector and the at least one of the one or more embedded objects, and (iii) a size of the at least one of the one or more embedded objects.

7. The system of claim 1, wherein a direction of emission of the radiation from the first radiation source is substantially orthogonal to a direction of emission of the radiation from the second radiation source.

8. A method comprising:
  detecting, by a first detector, first radiation from a first radiation source during irradiation of a medium, wherein the medium includes one or more embedded objects;
  receiving first data associated with the detected first radiation from the first detector, the receiving the first data including determining, based on the first data, a first angle associated with at least one of the one or more embedded objects;
  detecting, by a second detector oriented substantially orthogonally to the first detector, second radiation from a second radiation source located substantially orthogonally to the first radiation source during irradiation of the medium;
  receiving second data associated with the detected second radiation from the second detector, the receiving the second data including determining, based on the second data, a second angle associated with at least one of the one or more embedded objects; and
  determining, by one or more computers, a location of at least one of the one or more embedded objects based on the received first data and the received second data, the location being relative to the medium, the determining the location including:
    determining a distance between the first radiation source and the second radiation source;
    determining a first coordinate based on a first ratio of (i) the distance between the first radiation source and the second radiation source and (ii) a first function of the first angle and the second angle; and
    determining a second coordinate based on a second ratio of (i) the distance between the first radiation source and the second radiation source and a second function of the first angle and (ii) the first function of the first angle and the second angle.

9. The method of claim 8, wherein the location comprises a first coordinate and a second coordinate, the first coordinate being associated with a first dimension and the second coordinate being associated with a second dimension, the first dimension and the second dimension being substantially orthogonal.

10. The method of claim 8, wherein the location comprises a first coordinate and a second coordinate, the first coordinate and the second coordinate being Cartesian coordinates.

11. The method of claim 8, wherein the first radiation source and the second radiation source produce X-rays.

12. The method of claim 8, wherein the first radiation source and the second radiation source are neutron sources.

13. The method of claim 8, comprising:
  determining a first magnification error based upon (i) a distance between the first detector and the first radiation source, (ii) a distance between the first detector and the at least one of the one or more embedded objects, and (iii) a size of the at least one of the one or more embedded objects; and
  determining a second magnification error based upon (i) a distance between the second detector and the second radiation source, (ii) a distance between the second detector and the at least one of the one or more embedded objects, and (iii) a size of the at least one of the one or more embedded objects.

14. The method of claim 8, wherein a direction of emission of the radiation from the first radiation source is substantially orthogonal to a direction of emission of the radiation from the second radiation source.

15. A system comprising:
  a first radiation source;
  a first detector configured to:
    detect first radiation from the first radiation source during irradiation of a medium, wherein the medium includes one or more embedded objects;
  a second radiation source oriented substantially orthogonally to the first radiation source;
  a second detector located substantially orthogonally to the first detector configured to:
    detect second radiation from the second radiation source during irradiation of the medium; and
  one or more computers and one or more storage devices storing instructions that are operable, when executed by the one or more computers, to cause the one or more computers to perform operations comprising:
    receiving first data from the first detector, the first data associated with the detected first radiation;
    receiving second data from the second detector, the second data associated with the detected second radiation;
    determining a location of at least one of the one or more embedded objects based on the detected first data and the detected second data, the location being relative to the medium;
    determining a first magnification error based upon (i) a distance between the first detector and the first radiation source, (ii) a distance between the first detector and the at least one of the one or more embedded objects, and (iii) a size of the at least one of the one or more embedded objects; and
    determining a second magnification error based upon (i) a distance between the second detector and the second radiation source, (ii) a distance between the second detector and the at least one of the one or more embedded objects, and (iii) a size of the at least one of the one or more embedded objects.

* * * * *